US011241465B2

(12) United States Patent
Michalow et al.

(10) Patent No.: US 11,241,465 B2
(45) Date of Patent: Feb. 8, 2022

(54) COMPOSITIONS AND METHODS FOR SKIN TREATMENTS

(71) Applicant: ES BIOSOLUTIONS, INC., Irvine, CA (US)

(72) Inventors: Andrew H. Michalow, Mission Viejo, CA (US); Michael G. Goldfeld, Escondido, CA (US); John W. Baldridge, Newport Beach, CA (US); Alexander E. Michalow, Bourbonnais, IL (US)

(73) Assignee: ES BIOSOLUTIONS, INC., Irvine, CA (US)

( * ) Notice: Subject to any disclaimer, the term of this patent is extended or adjusted under 35 U.S.C. 154(b) by 0 days.

(21) Appl. No.: 15/925,489

(22) Filed: Mar. 19, 2018

(65) Prior Publication Data

US 2018/0264057 A1    Sep. 20, 2018

Related U.S. Application Data

(60) Provisional application No. 62/473,509, filed on Mar. 20, 2017, provisional application No. 62/621,458, filed on Jan. 24, 2018.

(51) Int. Cl.
| | | |
|---|---|---|
| *A61K 36/064* | (2006.01) | |
| *A61P 17/04* | (2006.01) | |
| *A61P 17/00* | (2006.01) | |
| *A61P 17/06* | (2006.01) | |
| *A61K 9/00* | (2006.01) | |

(52) U.S. Cl.
CPC .......... *A61K 36/064* (2013.01); *A61K 9/0014* (2013.01); *A61P 17/00* (2018.01); *A61P 17/04* (2018.01); *A61P 17/06* (2018.01)

(58) Field of Classification Search
CPC ..... A61K 36/064; A61K 9/0014; A61P 17/04; A61P 17/06; A61P 17/00
See application file for complete search history.

(56) References Cited

U.S. PATENT DOCUMENTS

| | | |
|---|---|---|
| 2,320,478 A | 6/1943 | Sperti |
| 4,540,571 A | 9/1985 | Schimanski |
| 4,942,031 A | 7/1990 | Levin |
| 5,023,090 A | 6/1991 | Levin |
| 5,356,874 A | 10/1994 | Bentley |
| 5,397,770 A | 3/1995 | Levin et al. |

(Continued)

FOREIGN PATENT DOCUMENTS

| | | | |
|---|---|---|---|
| EP | 0729750 A1 * | 9/1996 | ........... A61K 31/522 |
| JP | 50549545 B2 | 10/2012 | |

(Continued)

OTHER PUBLICATIONS

International Search Report and Wirtten Opinion issued in PCT/US2018/023164 dated May 14, 2018.

(Continued)

*Primary Examiner* — Jana A Hines
(74) *Attorney, Agent, or Firm* — Acuity Law Group, PC; Michael A. Whittaker

(57) ABSTRACT

The present invention relates to compositions of therapeutic yeast extracts for treatment of inflammatory conditions, methods of production of those extracts and methods of treating inflammatory skin/tissue afflictions.

21 Claims, 5 Drawing Sheets

(56) References Cited

U.S. PATENT DOCUMENTS

| | | | |
|---|---|---|---|
| 5,602,183 | A | 2/1997 | Martin et al. |
| 5,643,587 | A | 7/1997 | Scancarella et al. |
| 5,646,190 | A | 7/1997 | Martin |
| 5,658,956 | A | 8/1997 | Martin et al. |
| 5,676,956 | A | 10/1997 | Duffy et al. |
| 5,776,441 | A | 7/1998 | Scancarella et al. |
| 6,461,857 | B1 | 10/2002 | Scholz et al. |
| 6,858,212 | B2 | 2/2005 | Scholz et al. |
| 7,217,417 | B2 | 5/2007 | Knapp et al. |
| 7,476,529 | B2 | 1/2009 | Podella et al. |
| 7,645,730 | B2 | 1/2010 | Baldridge et al. |
| 7,659,237 | B2 | 2/2010 | Baldridge et al. |
| 7,759,301 | B2 | 7/2010 | Baldridge et al. |
| 8,114,422 | B2 | 2/2012 | Fujii et al. |
| 8,410,055 | B2 | 4/2013 | Li et al. |
| 8,575,106 | B2 | 11/2013 | Santhanam |
| 8,628,783 | B2 | 1/2014 | Iino et al. |
| 2011/0052517 | A1* | 3/2011 | Santhanam .............. A61P 17/10 424/62 |
| 2013/0287715 | A1 | 10/2013 | Justen et al. |

FOREIGN PATENT DOCUMENTS

| | | | | |
|---|---|---|---|---|
| WO | WO-2008059523 | A2 * | 5/2008 | .............. C07K 14/54 |
| WO | WO-2012072951 | A1 * | 6/2012 | ................ A61K 8/99 |

OTHER PUBLICATIONS

Abidi et al., Lifitegrast: A novel drug for treatment of dry eye disease. J Pharmacol Pharmacother. Oct.-Dec. 2016;7(4):194-198.

Ackerman et al., Ocular itch associated with allergic conjunctivitis: latest evidence and clinical management. Ther Adv Chronic Dis. Jan. 2016; 7(1):52-67.

Adami and Coruzzi, The Histamine H4 Receptor: A Novel Target for Safe Anti-inflammatory Drugs? Gastro Open J. 2014; 1(1):7-12.

Albrecht and Dittrich, Expression and function of histamine and its receptors in atopic dermatitis. Mol Cell Pediatr. Dec. 2015;2(1):16 (8 pages).

Allen et al., Adaptive and Innate Transforming Growth Factor β Signaling Impact Herpes Simplex Virus 1 Latency and Reactivation. J Virol. Nov. 2011;85(21):11448-11456.

Arican et al., Oxidative Stress in Patients With Acne Vulgaris. Mediators Inflamm. Dec. 14, 2005;2005(6):380-384.

Ashida et al., Histamine H1 and H2 Receptor Antagonists Accelerate Skin Barrier Repair and Prevent Epidermal Hyperplasia Induced by Barrier Disruption in a Dry Environment. J Invest Dermatol Feb. 2001;116(2):261-265.

Atalay et al., Heat Shock Proteins in Diabetes and Wound Healing. Curr Protein Pept Sci. Feb. 2009; 10(1): 85-95.

Babyatsky et al., Expression of Transforming Growth Factors alpha and beta in Colonic Mucosa in Inflammatory Bowel Disease. Gastroenterology. Apr. 1996;110(4):975-984.

Balakumar and Arasaratnam, Osmo-, Thermo- and Ethanol-Tolerances of *Saccharomyces cerevisiae* S1. Braz J Microbiol. Jan. 2012;43(1):157-166.

Barabutis and Catravas, Anti-Inflammatory Activity of Hsp90 Inhibitors in the Human Vasculature. Med Surg Urol 2013;2(1):e104 (2 pages).

Bayarjargal et al., Utilization of spent brewer's yeast *Saccharomyces cerevisiae* for the production of yeast enzymatic hydrolysate, Mongolian J Chem. 2011;12(38):88-91.

Bentley et. al., Peptides from live yeast cell derivative stimulate wound healing. Arch Surg. May 1990;125(5):641-646.

Bid and Kerk, BET bromodomain inhibitor (JQ1) and tumor angiogenesis. Oncoscience. Nov. 23, 2016;3(11-12):316-317.

Bilal et al., A Systematic Review and Meta-analysis of Efficacy and Safety of Novel Interleukin Inhibitors in the Management of Psoriatic Arthritis. J Clin Rheumatol. Jan. 2018;24(1):6-13 accessed online at: https://www.medscape.com/viewarticle/890997_1 (9 pages).

Bin et al., The Itchy scalp—scratching for an explanation, Exp Dermatol. Dec. 2011;20(12):959-968.

Bitar and Al-Mulla, Ros constitute a convergence nexus in the development of IGF1 resistance and impaired wound healing in a rat model of type 2 diabetes. Dis Model Mech. May 2012;5(3):375-388.

Boehncke et al., Differential expression of heat shock protein 70 (HSP70) and heat shock cognate protein 70 (HSC70) in human epidermis Arch Dermatol Res. 1994;287(1):68-71 (abstract only).

Champagne et.al., Interaction between pH, autolysis promoters and bacterial contamination on the production of yeast extracts. Food Res Internl 1999;32:575-583.

Coimbra and Santos-Silva, A specific molecular signature for psoriasis and eczema. Ann Transl Med. Apr. 2015;3(6):76 (3 pages).

Conley et al., Substance P (Neurokinin 1) Receptor Antagonists Enhance Dorsal Raphe Neuronal Activity. J Neurosci. Sep. 1, 2002;22(17):7730-7736.

Coondoo, The Role of Cytokines in The Pathomechanism of Cutaneous Disorders. Indian J Dermatol. Mar. 2012;57(2):90-96 (12 pages).

Doss et al., Heat Shock Protein-70 Expression in Vitiligo and its Relation to the Disease Activity. Indian J Dermatol. Jul.-Aug. 2016;61(4):408-412.

Drosou et al., Antiseptics on Wounds: An Area of Controversy. Wounds 2003; 15(5): 20 pages.

Effector mechanisms in allergic reactions. In Immunobiology: The Immune System in Health and Disease. 5th edition, Janeway et al., New York: Garland Science; 2001. Accessed online at https://www.ncbi.nlm.nih.gov/books/NBK27112(10 pages).

El Din et al., Immunohistochemical Expression of Heat Shock Protein 70 in Psoriasis Vulgaris. NY Sci J 2010;3(4):112-116.

Friedlander, Fibrosis and diseases of the eye J Clin Invest. Mar. 2007;117(3):576-586.

Ghoreishi, Heat shock proteins in the pathogenesis of inflammatory skin diseases. J Med Dent Sci. Jun. 2000;47(2):143-150.

Gibney et al., Yeast metabolic and signaling genes are required for heat-shock survival and have little overlap with the heat-induced genes. Proc Natl Acad Sci U S A. Nov. 12, 2013; 110(46): E4393-E4402.

Gillard et al., DMF, but not other fumarates, inhibits NF-κB activity in vitro in an Nrf2-independent manner. J Neuroimmunol. Jun. 15, 2015;283:74-85.

Gohel et al., The relationship between cytokine concentrations and wound healing in chronic venous ulceration. J Vasc Surg. Nov. 2008;48(5):1272-1277.

Goldenberg, Optimizing Treatment Approaches in Seborrheic Dermatitis. J Clin Aesthet Dermatol. Feb. 2013;6(2):44-49.

Gottlicher et al., Valproic acid defines a novel class of HDAC inhibitors inducing differentiation of transformed cells. EMBO J. Dec. 17, 2001; 20(24): 6969-6978.

Guo and Dipietro, Factors Affecting Wound Healing. J Dent Res. Mar. 2010;89(3):219-229.

Han et al., The Pro-inflammatory Role of TGFβ1: A Paradox? Int J Biol Sci. 2012;8(2):228-235.

Heat shock protein. Wikipedia Definition accessed online at: https://en.wikipedia.org/wiki/Heat_shock_protein, last edited on Jul. 26, 2018 (11 pages).

Herbert et al., NMR Structure of Hsp12, a Protein Induced by and Required for Dietary Restriction-Induced Lifespan Extension in Yeast. PLoS One. 2012;7(7):e41975 (12 pages).

Hong et al., Stimulatory effects of histamine on migration of nasal fibroblasts. Int Forum Allergy Rhinol. Oct. 2015;5(10):923-928 accessed online at: http://onlinelibrary.wiley.com/doi/10.1002/alr.21555/abstract (abstract only).

Huang et al., Mite Allergen Induces Allergic Dermatitis with Concomitant Neurogenic Inflammation in Mouse. J Invest Dermatol. Aug. 2003;121(2):289-293.

Ibrahim and Kairo, Effect of sub-clinical endometritis on miRNAs expression profile of endometrial and oviductal epithelium and its implication of early embryonic development. Inaugural Disssertation for Institut für Tierwissenschaften, Abt. Tierzucht und Tierhaltung

(56) References Cited

OTHER PUBLICATIONS der Rheinischen Friedrich—Wilhelms—Universität Bonn Mar. 9, 2015. Accessed online at: http://hss.ulb.uni-bonn.de/2015/3960/3960.pdf (124 pages).
Ikoma et al., The neurobiology of itch. Nat Rev Neurosci. Jul. 2006;7(7):535-547.
Inada et al., Histamine H1 and H4 receptor expression on the ocular surface of patients with chronic allergic conjunctival diseases. Allergol Int. Oct. 2017;66(4):586-593 http://www.sciencedirect.com/science/article/pii/S1323893017300370.
Jee et al., Antioxidant and Inflammatory Cytokine in Tears of Patients With Dry Eye Syndrome Treated With Preservative-Free Versus Preserved Eye Drops. Invest Ophthalmol Vis Sci. Jul. 3, 2014;55(8):5081-5089.
Jensen et al., Anti-Inflammatory Properties of a Dried Fermentate In Vitro and In Vivo. J Med Food. Mar. 2015;18(3):378-384.
Jian et al., TRPV1 and PLC Participate in Histamine H4 Receptor-Induced Itch. Neural Plast. 2016,2016:1682972 (9 pages).
Jonak et al., Heat shock proteins in the skin. Int J Cosmet Sci. Aug. 2006;28(4):233-241.
Kadam et al., Role of Oxidative Stress in Various Stages of Psoriasis . Indian J Clin Biochem. Oct. 2010;25(4):388-392.
Kakeda et al., Increased expression of heat shock protein 90 in keratinocytes and mast cells in patients with psoriasis. J Am Acad Dermatol. Apr. 2014;70(4):683-690.e1. doi: 10.1016/j.jaad.2013.12.002. Epub Feb. 9, 2014. http://www.ncbi.nlm.nih.gov/pubmed/24521827 (abstract only).
Kastl et al., TNF-α mediates mitochondrial uncoupling and enhances ROS-dependent cell migration via NF-κB activation in liver cells. FEBS Lett. Jan. 3, 2014;588(1):175-183.
Kelhälä et al., IL-17/Th17 Pathway Is Activated in Acne Lesions. PLoS One. 2014; 9(8): e105238 (18 pages).
Kennedy and Silver, Neuroimmune Signaling: Cytokines and the Central Nervous System. In: Pfaff, Volkow (eds) Neuroscience in the 21st Century. Springer, New York, NY Jul. 2016:1-41. Accessed online at: https://link.springer.com/referenceworkentry/10.1007%2F978-1-4614-6434-1_174-2 (10 pages).
Khan et al., Mitochondrial Uncoupler Prodrug of 2,4-Dinitrophenol, MP201, Prevents Neuronal Damage and Preserves Vision in Experimental Optic Neuritis. Oxid Med Cell Longev. 2017;2017:7180632 (11 pages).
Khmaladze et al., Reactive Oxygen Species in Psoriasis and Psoriasis Arthritis: Relevance to Human Disease. Int Arch Allergy Immunol. 2015;166(2):135-149.
Kim et al., Neural regulation of cancer: from mechanobiology to inflammation. Clin Transl Immunology. May 13, 2016;5(5):e78 (9 pages).
Kollipara et al., Interleukin-23 in the Pathogenesis and Treatment of Psoriasis Center for Clinical Studies, Skin Therapy Lett. Mar.-Apr. 2015;20(2):1-4 (6 pages).
Kono et al., Proteasomal Degradation Resolves Competition between Cell Polarization and Cellular Wound Healing. Cell. Jul. 6, 2012;150(1):151-164.
Krafts, Tissue repair: The hidden drama. Organogenesis. Oct.-Dec. 2010;6(4):225-233.
Krystel-Whittemore et al., Mast Cell: A Multi-Functional Master Cell. Front Immunol. Jan. 6, 2016;6:620 (12 pages).
Larjava et al., Exploring Scarless Healing of Oral Soft Tissues. J Can Dent Assoc. 2011;77:b18 (5 pages).
Lippert et al., Human Skin Mast Cells Express H2 and H4, but not H3 Receptors. J Invest Dermatol. Jul. 2004;123(1):116-23.
Liu et al., Chapter 14: Toll-Like Receptors and Itch Toll-Like Receptors and Itch. In: Carstens E, Akiyama T, editors. Itch: Mechanisms and Treatment. Boca Raton (FL): CRC Press/Taylor & Francis; 2014. Chapter 14. (12 pages) Accessed online at: https://www.ncbi.nlm.nih.gov/books/NBK200916//.
Loo et al., Effects of Hydrogen Peroxide on Wound Healing in Mice in Relation to Oxidative Damage. PLoS One. 2012;7(11):e49215 (13 pages).
Majumdar et al., Altered expression of Tumor Necrosis Factor Alpha-Induced Protein 3 correlates with disease severity in Ulcerative Colitis. Sci Rep. Aug. 25, 2017;7(1):9420 (13 pages).
Man et al., Analysis of epithelial-mesenchymal transition markers in psoriatic epidermal keratinocytes. Open Biol. Aug. 2015; 5(8): 150032 (10 pages).
Meseguer et al., TRPA1 channels mediate acute neurogenic inflammation and pain produced by bacterial endotoxins. Nat Commun. 2014;5:3125 (14 pages).
Mijouin et al., Effects of a Skin Neuropeptide (Substance P) on Cutaneous Microflora. PLoS One. Nov. 8, 2013;8(11):e78773 (11 pages).
Millson and Piper, Insights from yeast into whether the rapamycin inhibition of heat shock transcription factor (Hsf1) can prevent the Hsf1 activation that results from treatment with an Hsp90 inhibitor. Oncotarget. Jul. 15, 2014;5(13):5054-5064.
Morano et al., The Response to Heat Shock and Oxidative Stress in *Saccharomyces cerevisiae*. Genetics. Apr. 2012;190(4): 1157-1195.
Nie et al., HSV-1 infection suppresses TGF-β1 and SMAD3 expression in human corneal epithelial cells. Mol Vis. Sep. 3, 2008;14:1631-1638.
Ohsawa and Hirasawa, The Role of Histamine H1 and H4 Receptors in Atopic Dermatitis: From Basic Research to Clinical Study. Allergol Int. Dec. 2014;63(4):533-542.
O'Mahony et al., Regulation of the immune response and inflammation by histamine and histamine receptors. J Allergy Clin Immunol. Dec. 2011;128(6):1153-1162.
Okada et al., TRPA1 is required for TGF-β signaling and its loss blocks inflammatory fibrosis in mouse corneal stroma. Lab Invest. Sep. 2014;94(9):1030-1041.
Okayama, Oxidative Stress in Allergic and Inflammatory Skin Diseases. Curr Drug Targets Inflamm Allergy. Aug. 2005;4(4):517-519 (abstract only).
Osterburg, Characterization of the LYCD-Dependent Transcriptional Response in the THP-1 Cell Culture Monocytes. Electronic Thesis or Dissertation. University of Cincinnati, 2005. Accessed online at: http://rave.ohiolink.edu/etdc/view?acc_num=ucin1123870203 (156 pages total).
Pelle et al., Identification of Histamine Receptors and Reduction of Squalene Levels by an Antihistamine in Sebocytes. J Invest Dermatol. May 2008; 128(5):1280-1285.
Penn et al., The role of the TGF-β family in wound healing, burns and scarring: a review. Int J Burns Trauma. 2012;2(1): 18-28.
Pickart et al., GHK-Cu may Prevent Oxidative Stress in Skin by Regulating Copper and Modifying Expression of Numerous Antioxidant Genes. Cosmetics 2015;2(3):236-247.
Piper et al., Induction of major heat-shock proteins of *Saccharomyces cerevisiae*, including plasma membrane Hsp30, by ethanol levels above a critical threshold. Microbiology. Nov. 1994;140 ( Pt 11):3031-3038.
Pirim et al., Expression of the 8 kDa Heat Shock Protein (Ubiquitin) in Psoriasis. Turk J Med Sci 2001 ;31:69-72.
Podella et al., Yeast protein-surfactant complexes uncouple microbial electron transfer and increase transmembrane leak of protons. J Appl Microbiol. Jan. 2009;106(1):140-148.
Potenzieri and Undem, Basic Mechanisms of Itch, Clin Exp Allergy. Jan. 2012;42(1):8-19.
Powell, From leaf to itch. Sep. 6, 2016 accessed online at: https://news.harvard.edu/gazette/story/2016/09/from-leaf-to-itch/ (6 pages).
Praekelt and Meacock, HSP12, a new small heat shock gene of *Saccharomyces cerevisiae*: analysis of structure, regulation and function. Mol Gen Genet. Aug. 1990;223(1):97-106 (abstract only).
Puusa, Research shows inflammation causes acne. Natural News Mar. 7, 2011, 2011 accessed online at: http://www.naturalnews.com/031605_inflammation_acne.html.
Rajan and Murray, The duplicitous nature of inflammation in wound repair. Wound Practice and Research Aug. 2008;16(3):122-129.
Ranganathan and Mukhopadhyay, Dandruff: The Most Commercially Exploited Skin Disease. Indian J Dermatol. Apr.-Jun. 2010;55(2):130-134 (10 pages).
Reich and Szepietowski, Clinical Aspects of Itch: Psoriasis. In: Carstens E, Akiyama T, editors. Itch: Mechanisms and Treatment.

(56) References Cited

OTHER PUBLICATIONS

Boca Raton (FL): CRC Press/Taylor & Francis; 2014. Chapter 4. (12 pages) Accesssed online at: https://www.ncbi.nlm.nih.gov/books/NBK200930/.
Rodero and Khosrotehrani, Skin wound healing modulation by macrophages. Int J Clin Exp Pathol. Jul. 25, 2010;3(7):643-653.
Romaschenko et al., Low concentrations of uncouplers of oxidative phosphorylation prevent inflammatory activation of endothelial cells by tumor necrosis factor. Biochemistry (Mosc). May 2015;80(5):610-619.
Rossbach et al., Histamine H1, H3 and H4 receptors are involved in pruritus. Neuroscience. Sep. 8, 2011;190:89-102.
Schlemm et al., Medicinal yeast extracts. Cell Stress Chaperones. Sep. 1999;4(3):171-176.
Seppä, Regulation of Heat Shock Response in Yeast and Mammalian Cells. Institute of Biotechnology and Faculty of Biosciences Department of Biological and Environmental Sciences Division of Biochemistry and Helsinki Graduate School in Biotechnology and Molecular Biology. Academic Dissertation Sep. 2005 (64 pages). Downloaded at: http://ethesis.helsinki.fi/julkaisut/eri/biote/vk/seppa/regulati.pdf.
Shim and Oh, Histamine-induced itch and its relationship with pain. Mol Pain. Jul. 31, 2008;4:29.
Siggers and Lesser, The Yeast *Saccharomyces cerevisiae*: A Versatile Model System for the Identification and Characterization of Bacterial Virulence Proteins. Cell Host Microbe. Jul. 17, 2008;4(1):8-15.
Singarapu et al., Structural Characterization of Hsp12, the Heat Shock Protein from *Saccharomyces cerevisiae*, in Aqueous Solution Where It Is Intrinsically Disordered and in Detergent Micelles Where It Is Locally α-Helical. J Biol Chem. Dec. 16, 2011;286(50):43447-43453.
Spergel, Immunology and Treatment of Atopic Dermatitis. Am J Clin Dermatol. 2008;9(4):233-234, accessed online at: http://www.medscape.com/viewarticle/588548_4 (16 pages).
Ständer et al., Treatment of pruritic diseases with topical calcineurin inhibitors. Ther Clin Risk Manag. Jun. 2006;2(2):213-218.
Stanway, Causes of atopic dermatitis. Found on DermNet accessed online at: http://www.dermnetnz.org/dermatitis/atopic-causes.html, Feb. 2004 (6 pages).
Stern et al., Dry Eye as a Mucosal Autoimmune Disease. Int Rev Immunol. Feb. 2013;32(1):19-41.
Sun et al., An extended set of yeast-based functional assays accurately identifies human disease mutations. Genome Res. May 2016;26(5):670-680.
Sutherland, Why We Itch: How it arises is only now becoming clear. Scientific American, May 2016:40-43.
Tanghetti, The Role of Inflammation in the Pathology of Acne. J Clin Aesthet Dermatol. Sep. 2013;6(9):27-35.
Tanguler and Erten, Utilisation of spent brewer's yeast for yeast extract production by autolysis: The effect of temperature. Food and Bioproducts Processing Dec. 2008;86(4):317-321.
Tecilazich et al., Role of Endothelial Progenitor Cells and Inflammatory Cytokines in Healing of Diabetic Foot Ulcers. PLoS One. Dec. 16, 2013;8(12):e83314.
The skin-specific proteome. Human Protein Atlas version 18, Release date: Dec. 1. 2017 accessed online at: http://www.proteinatlas.org/humanproteome/skin (6 pages).
Thiboutot et al., IL-17: A Key Player in the P. acnes Inflammatory Cascade? J Invest Dermatol. Feb. 2014;134(2):307-310.
Thurmond, The histamine H4 receptor: from orphan to the clinic. Front Pharmacol. Mar. 31, 2015;6:65 (11 pages).
UC Davis, New Molecular Target Could Help Ease Asthma. ScienceDaily. Mar. 7, 2018 (4 pages) accessed online at: https://www.alnmag.com/news/2018/03/new-molecular-target-could-help-ease-asthma.
UVA et al., Mechanisms of Action of Topical Corticosteroids in Psoriasis. Int J Endocrinol. 2012;2012:561018, (17 pages).
Velculescu et al., Characterization of the Yeast Transcriptome. Cell. Jan. 24, 1997;88(2):243-251.
Verghese et al., Biology of the Heat Shock Response and Protein Chaperones: Budding Yeast (*Saccharomyces cerevisiae*) as a Model System. Microbiol Mol Biol Rev. Jun. 2012;76(2):115-158.
Versele et al., Sex and sugar in yeast: two distinct GPCR systems. EMBO Rep. Jul. 2001;2(7):574-579.
Vidal Magalhães et al., Heat Shock Proteins (HSP): dermatological implications and Perspectives. Eur J Dermatol. Jan.-Feb. 2012;22(1):8-13.
Villa et al., Feather keratin hydrolysates obtained from microbial keratinases: effect on hair fiber. BMC Biotechnol. Feb. 18, 2013;13:15 (11 pages).
Vosti and Joslyn, Autolysis of Baker's Yeast, Department of Food Technology, Appl Microbiol. Mar. 1954;2(2):70-78.
Wang et al., Effects of treatment with an Hsp90 inhibitor in tumors based on 15 phase II clinical trials. Mol Clin Oncol. Sep. 2016; 5(3):326-334.
Wei and Asbell, The Core Mechanism of Dry Eye Disease (DED) Is Inflammation . Eye Contact Lens. Jul. 2014;40(4):248-256.
Weichhart et al., Inhibition of mTOR blocks the anti-inflammatory effects of glucocorticoids in myeloid immune cells. Blood. Apr. 21, 2011;117(16):4273-4283.
Welker et al., Hsp12 Is an Intrinsically Unstructured Stress Protein that Folds upon Membrane Association and Modulates Membrane Function. Mol Cell. Aug. 27, 2010;39(4):507-520.
Weller et al., Nitric Oxide Is Generated on the Skin Surface by Reduction of Sweat Nitrate. J Invest Dermatol. Sep. 1996;107(3):327-331.
Wilson and Esposito, Interleukin-1: A master regulator of the corneal response to injury. Exp Eye Res. Aug. 2009;89(2):124-125.
Woodfolk, Allergy and Dermatophytes, Clin Microbiol Rev. Jan. 2005;18(1):30-43.
Xu et al., Histone deacetylase inhibitors: molecular mechanisms of action. Oncogene. Aug. 13, 2007;26(37):5541-5552.
Yale University, Langerhans Cells Regulate Immune Reactions In The Skin. ScienceDaily. Dec. 20, 2005 (4 pages). Accessed online at: https://www.sciencedaily.com/releases/2005/12/051220000731.htm.
Zakharova et al., Low concentration of uncouplers of oxidative phosphorylation decreases the TNF-induced endothelial permeability and lethality in mice. Biochim Biophys Acta. Apr. 2017;1863(4):968-977.
Zheng et al., Evaluation of the Transforming Growth Factor β Activity in Normal and Dry Eye Human Tears by CCL-185 Cell Bioassay. Cornea. Sep. 2010;29(9):1048-1054.
Lupo and Cole, "Cosmeceutical peptides", Dermatologic Therapy, vol. 20, 2007, 343-349.

* cited by examiner

FIG. 3

COMPOSITIONS AND METHODS FOR SKIN TREATMENTS

The present invention claims priority to U.S. Provisional Patent Application 62/473,509, filed Mar. 20, 2017; and U.S. Provisional Patent Application 62/621,458, filed Jan. 24, 2018; each of which is hereby incorporated by reference in its entirety including all tables, figures, and claims.

FIELD OF THE INVENTION

The present invention is in the field of the yeast-derived products for topical applications in treatment of human and animal tissue conditions associated with inflammation and itch, including, but not limited to lesions, abnormal growth and immune-compromised situations.

BACKGROUND OF THE DISCLOSURE

A broad range of ingredients derived from natural sources have been suggested for various topical applications, including cosmetic and dermatological uses. One important source of skin care ingredients is yeast, namely and especially, although not limited to, Bakers and Brewers yeasts, *Saccharomyces cerevisiae*, due to a long history of their consumption by humans and overwhelming data supporting that their derivative products are non-toxic and safe.

Liquid, cream, gel and paste-like topical compositions for skin care are generally a combination of various ingredients optimized for effects that are used for cleansing and sanitizing, assist in uptake by the skin of various biologically active compounds that improve their condition, help to regulate and/or reduce inflammations associated with itch and pain, assist in treatment of wounds and burns, and also address cosmetic issues, such as, hydrating/moisturizing of dry and scaly skin condition, as well as wrinkles and other manifestations of aging.

Yeast extracts are used as adjuvants for the treatment of certain skin conditions. Before the current invention, however, no yeast extract, in and of itself, with no additional active ingredients, has been developed that unequivocally shows the ability to mitigate inflammatory conditions for a wide range of conditions, both acute or chronic. In that regard, for the purposes of the current invention, the yeast extracts will be termed, "therapeutic yeast extracts."

One problem with the current yeast extract-based skin care products, is that the extracts may contain constituents and added ingredients that may affect the user negatively, depending on the condition, or specific use, or the type of tissue to be treated. They can either produce adverse events or in cosmetic or topical applications may exhibit noxious odors. Or, beneficial constituents may not be at levels that would deliver a therapeutic effect with yeast extracts that have been proposed previous to the current invention. Where uses are applicable for yeast extracts, developers are then forced to introduce additional ingredients into the product to provide a therapeutic effect, or to mitigate the adverse effects or, in some instances, to mask inherent odors of a yeast extract. Compositions and methods disclosed herewith provide practical solutions to these problems and add new uses for the specially derived therapeutic yeast extracts.

Some of the features in yeast extracts noted above can limit their potential for use in applications where sensitive or compromised skin or tissues are involved. Many yeast extracts, like a live yeast cell derivative ("LYCD"), are produced using harsh conditions and chemicals such as alcohol at high temperatures, strong acids or alkali, or peroxides, which may alter their chemical make-up and properties. Existing patents and literature do not generally address this potential issue. Nonetheless, LYCD yeast extract proteins in the size range greater than 6 kDa, up to 104 kDa, have been reported to assist in wound healing. Other studies do not support wound healing effect of LYCD. There are still other reports on the use of yeast extracts as adjuvants assisting in treatment of a limited range of skin conditions.

U.S. Pat. No. 5,023,090 (Levin) refers to the use of LYCD as an adjuvant combined with certain topically active medicinal agents.

U.S. Pat. No. 5,356,874 (Bentley) states that: " . . . the wound healing effects of LYCD are due to a mixture of peptides and/or small proteins with molecular weights ranging between about 6,000 daltons and about 17,000 daltons . . . " and that low molecular weight proteins may be removed, while higher molecular weight species concentrated.

U.S. Pat. No. 5,646,190 (Martin) states that results using a LYCD formulation did not exhibit wound healing compared to a similar formulation without LYCD, which contradicts Bentley.

U.S. Pat. No. 5,776,441 (Scancarella) refers to growing yeast and then using UV radiation to stress the yeast, which is then lysed with a proteolytic enzyme, following which insoluble materials are removed from the liquid extract solution.

U.S. Pat. No. 6,858,212 (Scholz) refers to a yeast extract produced using a sublethal amount hydrogen peroxide to stress yeast until the yeast shows signs of being disrupted, where an enzyme is added to lyse the cells, stopping fermentation, and "has significantly increased amounts of 15, 25 and 55 kDa molecular weight products compared to a Live Yeast Cell Derivative".

BRIEF DESCRIPTION OF THE INVENTION

It is an object of the invention to provide extracts derived from yeast that have been subjected to a post-fermentation process, where the insoluble solids from the yeast itself are removed from the final product.

Since metabolic paths in the skin may be similar to those in other body tissues, such as mucous membrane tissues, for the purposes of the current invention, the term "skin" shall mean the layer of tissue forming the natural outer covering of the body of a person or animal. Thus, for purposes of the present invention, skin includes, but is not limited to, the epidermis (and particularly the stratum cornium), dermis, subcutis, mucus membranes that are a continuous with the skin at various body openings such as the eyes, ears, inside the nose, inside the mouth, lip, the urethral opening, the vaginal opening, and the anus, and mucous membranes covering the surface of internal organs. Thus, treatments described herein will include topical treatments as well as enteral treatments and treatment of mucous membranes and in various human organs. Further, many yeast produced materials are homologous throughout the animal kingdom and the current invention further includes that the defined treatments are applicable to animals. For simplicity, the current invention will refer to human skin and tissues, but this does not limit their use in similar animal applications.

In a first aspect, the present invention provides compositions comprising a therapeutic extract from yeast that comprises: (a) an anti-inflammatory agent and an uncoupling agent that is active in animal, preferably mammalian, and most preferably human, cells. In various embodiments, the anti-inflammatory agent(s) present in the composition comprise an anti-itch agent, a GPCR antagonist agent, and/or a cytokine receptor agonist agent. In certain embodiments, the composition provides broad suppression of immunoinflammatory markers, as described hereinafter. For the purposes of the current invention the term "receptor antagonist" should be considered to be synonymous with "receptor antagonist agent" with respect to the composition of the current invention.

Preferably, the yeast is *Saccharomyces ceverisiae*.

In certain embodiments the anti-inflammatory agent or the anti-itch agent comprises a GPCR antagonist agent, preferably a histamine receptor antagonist agent, and most preferably an antagonist for one or more of H1R, H2R, H3R, and H4R, and/or a Substance P receptor antagonist.

In certain embodiments, the anti-inflammatory agent or the anti-itch agent comprises a cytokine receptor antagonist agent, and preferably an antagonist for a receptor of a cytokine selected from the group consisting of TNF-alpha, interferon-gamma, Granulocyte-macrophage colony-stimulating factor (GM-CSF), IL-1, IL-2, IL-4, IL-5, IL-6, IL-12, IL-13, IL-17, IL-22, IL-23, IL-31, IL-33.

As described hereinafter, the compositions of the present invention are antiproliferative to one or more of human primary B cells, endothelial cells, fibroblasts, and coronary artery smooth muscle cells in an in vitro cell based proliferation assay. In certain embodiments, the anti-inflammatory agent comprises one or more of an HSP90 inhibitor agent, a HDAC inhibitor agent and a BET inhibitor agent.

In various embodiments, the yeast extract comprises soluble constituents, is substantially colorless and odorless, and is devoid of insoluble materials that are separated from soluble matter, preferably by centrifugation. In the foregoing embodiments, the GPCR antagonist agent(s) and/or cytokine receptor antagonist agent(s) is/are preferably soluble in the yeast extract. In various embodiments, 95%, and preferably 98%, of GPCR antagonist agent(s) and/or cytokine receptor antagonist agent(s) present in the yeast extract is/are under a molecular weight of about 4,000 daltons.

In certain embodiments, the GPCR antagonist agent(s) and/or cytokine receptor antagonist agent(s) represent 90% or more of the soluble material in the composition, and preferably over 98%.

In preferred embodiments, the therapeutic yeast extract is substantially free of undesirable residue.

In certain embodiments, the composition further comprises: a preservative, an antimicrobial agent, an emollient, a fragrance, or combinations thereof.

In a related aspect, methods for producing the compositions of the present invention comprise (a) fermenting yeast, subjecting the yeast to at least two Fermentation procedures, (b) subjecting the yeast to a stress, (c) disrupting or lysing the yeast, (d) purifying the yeast to substantially remove undesirable residue, (e) separating insoluble material from the liquid soluble materials.

In certain embodiments the fermenting step includes at least one fermentation procedure under anaerobic conditions; and/or the fermenting step includes more than one fermentation procedure. The fermenting step can comprise a fermentation procedure at a temperature greater than 30° C., and the fermenting step comprises a total fermentation time of between 1 hour and to about 2 weeks.

In another aspect, the present invention provides a method of treating a subject in need of an anti-itch medication, comprising administering a composition as described herein. In various aspects, a subject is in need of the anti-itch medication due to the presence of eczema, psoriasis, atopic dermatitis, acne, dandruff, hemorrhoids, herpes, dry eye, eye allergies, or other inflammatory condition. In preferred aspects, the administration is topical.

In another aspect, the present invention provides a method of reducing an inflammatory condition in an individual comprising administering a composition as described herein. In various aspects, a subject is in need of reducing an inflammatory condition due to the presence of eczema, psoriasis, atopic dermatitis, acne, dandruff, hemorrhoids, herpes, dry eye, eye allergies, or other inflammatory condition. In preferred aspects, the administration is topical.

In another aspect, the present invention provides a method of treating a subject in need of skin improvement comprising administering a composition as described herein.

BRIEF DESCRIPTION OF THE FIGURES

FIG. 3 depicts a list of the cell types, disease context and list of biomarker readouts for the BioMAP Diversity PLUS panel.

DETAILED DESCRIPTION OF THE EMBODIMENTS

Figure 1A:
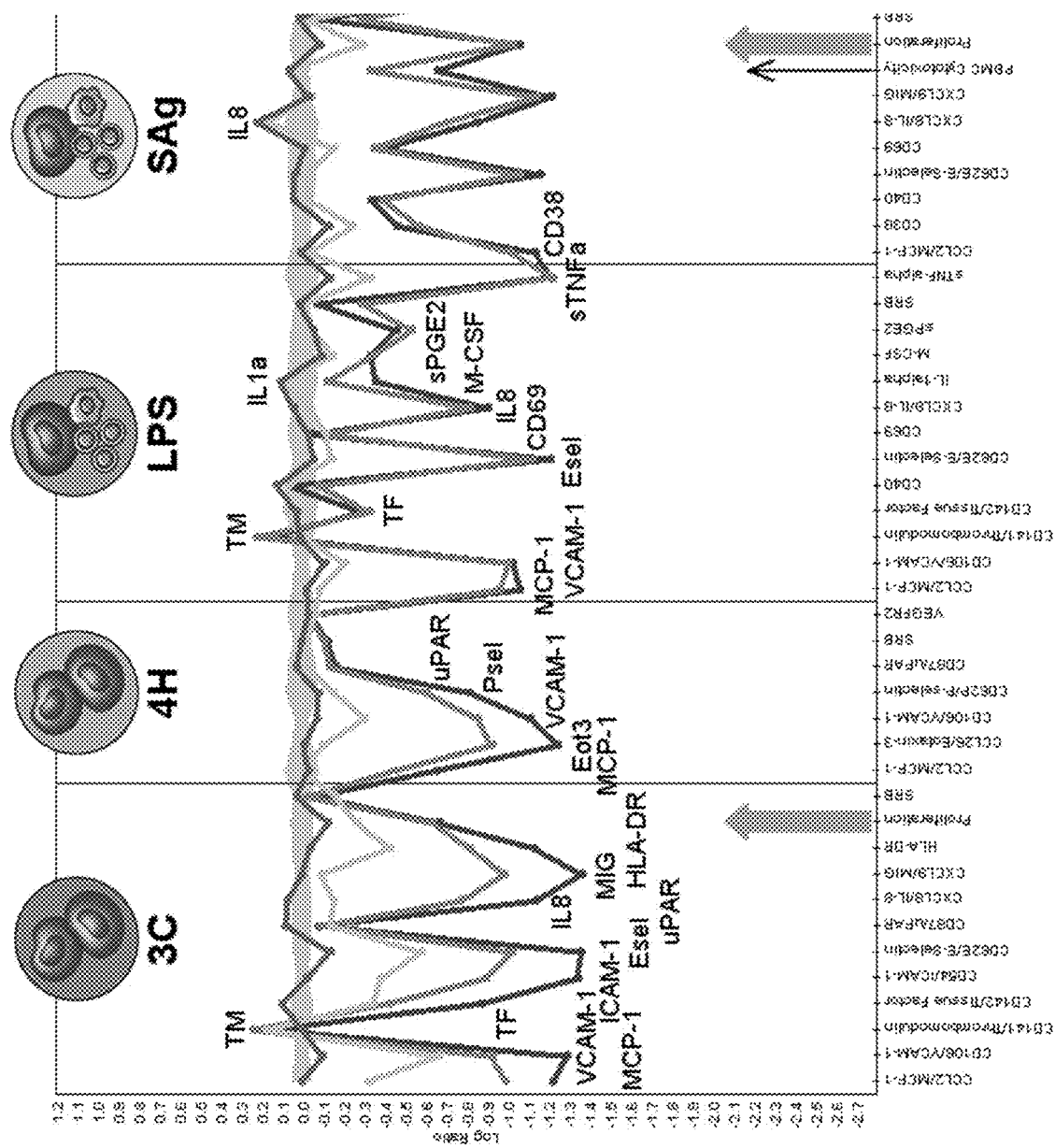
FIG. 1A depicts the results of phenotype profiling of a yeast extract composition of the present invention in the BioMAP Diversity PLUS panel BT, BF4T, BE3C, and CASM3C systems.

Disclosed herein are compositions of therapeutic yeast extracts for treatment of inflammatory conditions, methods of production of those extracts and methods of treating inflammatory skin/tissue afflictions. The therapeutic yeast extract compositions comprise anti-inflammatory agents, anti-itch agents and that are hypothesized to be activated, at least in part, by cell signaling receptor antagonists. Methods comprise the production parameters of the compositions and then identifying a subject in need of treatment and administering to the subject a formulation comprising the therapeutic yeast extracts. In some embodiments, the identifying and the administering steps are conducted by the subjects themselves. Finished formulations may further comprise other ingredients to either add features, or to enhance the features of the therapeutic yeast extracts.

The production of yeast extracts using fermentation techniques is, by definition, rooted in biological processes, starting with propagation of the yeast, typically as a first step. The specific parameters, including nutrients used in fermentation, will often alter the final composition of the end product. For example, notable differences in beer flavor, color, level of carbonation, appearance, etc. is observed, even when ingredients, temperatures, timing, and other process parameters are apparently similar. For the purposes of the current invention the term fermentation will be defined as a biological process for yeast, where the parameters of the Fermentation procedure(s) can include yeast propagation, the processing of the nutrients and other added chemicals by the yeast in the fermentation liquid, the conversion of nutrients and chemicals into desirable compounds, the production of desirable intracellular compounds, and where optimal conditions can be chosen from controlling and modifying parameters in the fermentation that include chemical levels, temperature, nutrients, pH, process time and post-Fermentation procedures. Fermentation can be done under aerobic or anaerobic conditions. Aerobic fermentation requires the presence and addition of oxygen, typically through forced aeration, but a blanket of air with agitation may suffice in some processes. Anaerobic conditions are such that oxygen is not being added to the system and when oxygen becomes depleted in the fermentation liquid, and where oxygen, namely through air, is not being added to a system that is closed or isolated from ambient air.

Though the yeast extracts of the present invention can be derived from virtually any yeast genus, a preferred yeast is Saccharomyces cerevisiae (bakers' yeast, or brewer yeast) as the source, the key benefit of which is their safety supported by thousands years of human consumption.

The function of previously described yeast derived ingredients for skin treatments has mostly been to provide an adjuvant effect with other materials, including biologically active ones. In one embodiment of the present invention, the therapeutic yeast extract is produced and purified in a way that contains yeast proteinaceous material (i.e. proteins, peptides and amino acids, and co-factors) in the amount constituting for up to about 98% of the total non-volatile solids in the product. In certain embodiments, the extract contains cell signaling antagonist agents which are predominantly under 4 kDa of molecular weight, and the material is fully water soluble (up at least 30%). In another embodiment, the cell signaling antagonist agents, and uncoupling agents that are active in animal, preferably mammalian, and most preferably human, cells, comprise over 98% of the total dissolved solids. In the embodiments, the total dissolved solids are presumed to be acting in totality as the antagonist agents. In certain embodiments, the therapeutic yeast extracts comprise molecular weight constituents, where a substantial amount above 4 KDa are not eliminated.

The present extracts are selected to provide efficacy in treatment of various inflammation-based afflictions with the results being better comfort, improved condition of the skin/tissue and reduction in the inflammation level. The afflictions and conditions that may be treated include, but are not limited to, inflammation-related and inflammation-based afflictions, such as itch, both chronic and acute, eczema, atopic dermatitis, psoriasis, hemorrhoids, acne, herpes, dandruff, athlete's feet, and wound healing. As described hereinafter, redness, scaly skin, itching and/or dry skin, or inflammatory conditions including mucous membranes, are reduced substantially by treatment with the therapeutic yeast extract and compositions containing the latter.

The therapeutic yeast extracts used in the compositions disclosed herein showed benefits in the treatment of the symptoms of the skin afflictions of a broadly diverse nature. Without wishing to be bound by a specific mechanism, it is believed that the afflictions that may be successfully ameliorated are based on dysregulated cell signaling that promote inflammatory conditions, but this hypothesis of a mechanism of action is not limiting to the features discovered, and other mechanisms may be in play.

The ability to produce purified yeast extracts with the cell signaling receptor antagonists is a key embodiment of the current invention. In vitro tests have shown that the therapeutic yeast extract act as an agent blocking (i.e., an antagonist) the cell receptor signaling sites, supporting the notion that this feature is, at least in part, responsible for the observed effects.

Yeast Extract Production

Exposing viable yeast to stress conditions during or after fermentation, regardless of the source and nature of stress, induces the yeast to express heat shock proteins ("HSPs", sometimes also called stress proteins) as a mechanism of protection and cell survival, ultimately to protect the cell, or to help promote the propagation of a family of cells, whether prokaryotic or eukaryotic. HSPs have been studied for decades and many different ones have been identified. These include the following, marked by molecular weight in kilodaltons (kDa): HSP10, HSP12, HsP 17, HsP20, HsP27, HsP36, HsP60, HsP 80, HsP90, HsP104 and some others. HSPs display high level of homology among a broad range of eukaryotes. They were also reported to be involved in pathogenesis of certain cancers and psoriasis.

While certain HSPs may be produced by yeast, they have not been shown to have direct effects on the wide range of inflammatory conditions discussed in the current invention. Since they can be active, in some embodiments it is beneficial to incorporate processes to eliminate the HSP's, as expressed by the yeast, and to help purify the extract and focus on retaining desired constituents. Nonetheless, the steps of stressing the yeast are important steps in the current invention as they are believed to be involved in the process of producing the desired materials. It is also important to eliminate the use of harsh conditions, such as those used to produce LYCD, where strong alkali and/or strong alcohol conditions are used to process that extract. Such strong chemicals may alter the chemistry to where desired constituents are not produced or may be chemically modified.

In addition, non-biological treatments may be added before, during or after the biological process proper. These secondary treatments may include mechanical disruption, separation and isolation techniques that induce of assist in the production of desired materials and eliminate undesirable materials.

Genetic recombinant yeast can be developed that have been optimized to produce the desired therapeutic yeast extract materials and can be used as the source to optimize the production of the therapeutic extracts.

Inflammation

Inflammation is a mechanism used by the human body to protect against stresses that include microbial attack, injury, systemic effects, environmental effects, allergies and other stress. That protection may rely on both pro-inflammatory and anti-inflammatory responses. In a perfect scenario, the two opposing responses are induced in a balanced way at appropriate stages of the protective, or healing process. When inflammatory conditions are dysregulated, or overexpressed, they can lead to many different types of afflictions. Some of these may be chronic, while others may be acute, as in allergic reactions. For the purposes of the current invention, the term "inflammatory condition" is synonymous with a dysregulated inflammatory condition, where a medical affliction is the result. Further, it pertains to the inflammatory response in a wound condition, which may be considered "normal" or compromised, for example, foot ulcers that are experienced by diabetics.

Inflammatory conditions are at the root of many skin disorders. Eczema, psoriasis, acne, atopic dermatitis, dandruff, seborrheic dermatitis, herpes, hemorrhoids, athlete's feet are examples where inflammatory conditions are a key underlying cause. The inflammatory response is complicated, with multiple pathways, hence the broad range of afflictions, though all can have one common denominator, dysregulated inflammatory response of the subject body. Common side effects of these conditions include itch and pain, dry and scaly skin/tissue, growths, poor healing of injuries, undesirable systemic effects, growth of undesirable tissues.

Inflammation is also a root cause of disorders of various mucous membranes, that include, but not limited by: dry eye, eye allergies, scleritis, uveitis, hemorrhoids, the nasal cavity, or inflammatory gum disorders, such as gingivitis. Similar pathways are related to these that are observed in skin disorders. In the treatment of mucous membranes, doses and ingredients may be vastly different that for skin, since they much better absorb topically applied ingredients. Skin is basically a protective organ with its key barrier function. Hence different ways of application and dose rates apply. A therapeutic yeast extract with broad inherent benefits should simplify and improve products targeting mucous membranes. The inherent safety of yeast derivative materials makes it most appropriate candidate for such treatments.

Corticosteroids are typical topical or oral products used to treat inflammatory conditions, whether for the skin or systemic issues. Steroids have many known undesirable side effects and features. In some instances, such as herpes simplex, a viral condition with inflammatory based symptoms, steroids exacerbate the condition instead of mitigating it. In that sense, an agent that has an anti-inflammatory effect in some situations, may not necessarily provide homeostasis, as in this example of herpes and steroids. Further, use of steroids in sensitive areas, such as the eyes requires special caution due to their side effects. Long-term use of steroids leads to a range of problems. Further, the body tends to become resistant to steroids, so that continuous use requires increasing their strength or dose rate, which only adds to the potential for severe side effects. For example, people with eczema who treat their skin with topical steroids may experience what is called "red skin syndrome," a debilitating condition.

Histamine

A common symptom of many skin disorders is itch. Despite the number of different causes, a common pathway leading to itch involves histamine. Histamine is a biological amine, a signaling molecule that regulates pathways in many different types of cells, including the skin. Histamine affects immune regulation, immunomodulation and inflammation, is involved with allergies and autoimmune diseases, and has long been known to be an inducer of itch. Further, it affects the cellular response to environmental and microbial stresses and attacks. It is involved in such a regulation of pathophysiological conditions in cellular events through binding to four types of histamine receptors—cell surface signaling sites that, upon histamine binding, generate a cellular response. Immune homeostasis is dependent on the interaction of histamine and its receptors. There are at least four types of histamine binding sites—membrane G Protein Coupled Receptors (GPCR): H1R, H2R, H3R and H4R, collectively HxR. These are differentially expressed in various types of cells, which potentially offers opportunities to treat numerous other conditions in the body. Histamine receptor "blockers," also called "antagonists," or antihistamines, have been developed to mitigate the afflictions related to overexpression of histamine with these receptor sites.

H1R blockers were the first type of histamine receptor antagonists to be commercialized. They are the classical "antihistamines" that have been applied to control allergic reactions. H1R antagonists are known to have an immediate effect on certain allergic reactions, that sometimes includes itch, but have not been shown to be effective in mitigating symptoms or pathology of chronic conditions that include eczema, atopic dermatitis, psoriasis, dandruff, and other chronic conditions, many of which exhibit itch as a symptom.

H1R antagonists, by themselves, have not been proven to relieve symptoms of acute itch, while H4R antagonists and their combinations with H1R antagonists were reported to provide relief from itch. H2R antagonists have been in commercial use for helping to control gastric acids. H3R is linked to the central nervous system and many related disorders. Many histamine receptor antagonists that are commercially available or in development exhibit side effects.

H2R antagonists have not been found to be involved in itch, or in eczema or atopic dermatitis. H1R and H2R have been found to be involved in the maintenance of skin barrier function and inflammation. Both types of histamine receptor antagonist inhibited epidermal hyperplasia with barrier disruption induced by acetone treatment in mice kept in dry conditions. Therefore, the histamine H1R and H2R receptors may contribute not only to skin barrier function but also to epidermal proliferation and/or inflammation.

H3R appears to have a role in itch and in allergic reactions. It is also involved in neurological, central nervous system pathways including the control of sleep. H3R antagonists and regulation of H2R have shown the potential to be used in the treatment of Alzheimer's disease.

H4R is known to be involved in itch pathology, including chronic conditions of the skin and eyes, such as eczema, psoriasis and eye allergies. Recombinant H4R antagonists have shown efficacy in mitigating the pathology of eczema and atopic dermatitis and possibly other chronic, inflammatory conditions. It is also thought that H1R and H4R act in concert in the itch response. H4R is useful as biomarkers of allergic inflammation on ocular surfaces.

HxR antagonists that are either commercial, or currently still in drug clinical trials, in general, have been shown to create undesirable side effects. A histamine receptor antagonist with no, or very little, side effects would be desirable to take advantage of the potential benefits of such agents. This latter feature, of being essentially non-toxic, is a key embodiment of the current invention that relies on the inherent safety of yeast extracts, as a class.

Cytokines

Cytokines are small proteins involved in cell signaling as they engage with their corresponding receptor sites. Antihistamine effects are often immediate and short term, while cytokines are, generally, responsible for longer-term events. This is a hypothesis and not limiting to the compositions of the current invention. Cytokine receptor antagonists are the target of many drug products. The drugs are typically ingested or injected, though some topical agents are being developed. Ingested and injected drugs, due to their inherent distribution throughout the body, tend to have undesirable side effects. Topical agents generally have fewer side effects but may be not as effective as the systemic treatments for certain afflictions, such as eczema, atopic dermatitis, psoriasis, etc., where systemic causes drive the affliction. Cytokines are also involved in the immune response and mitigating their effects could provide benefits to chronic health afflictions that go beyond skin by affecting certain tissues that are involved with the expression of such cytokines. Metastasis of many cancers is induced by cytokines. For example, in breast cancer study, IL-6 and TNF-alpha enabled breast cancer cells to adhere to endothelial wall, which was the foundation leading to metastasis. These cytokines then helped to set off the expression of other cytokines.

Cytokines are essentially pro-inflammatory, and thus typically termed inflammatory cytokines. They include, among others, tumor necrosis factor (TNF-α cachexin, or cachectin), Interleukin-1 (IL-1, alpha and beta), IL-2, IL-4, IL-5, IL-6, IL-12, IL-13, IL-17A, IL-22, IL-31, IL-33, and Inteferon-gamma and GM-CSF (granulocyte-macrophage colony-stimulating factor, that functions as a cytokine). The overexpression and/or dysregulation of the inflammatory cytokines are a part of the pathophysiology that is found in many inflammatory conditions. This further pertains to inflammation in wound healing, including, but not limited to, traumatic, surgical, chronic stasis and burn wounds. Dysregulation of cytokine or growth factor expression hinders acute healing of wounds, and blocking the excessive production of specific proinflammatory cytokines can lead to a path toward mitigating their effects. This can be done by administering agents that bind to their signal receptor sites, so as to reduce the overexpression of the corresponding pro-inflammatory proteins. This approach, targeting cell signal receptor sites, is the basis for the design of many drugs. For clarity and the use of terms in the current invention, the phrase "IL-X antagonist" is synonymous with it being called an antagonist, or blocker, of its corresponding receptor site(s), whereby the production of IL-X is hindered. Many of such antagonists are produced using recombinant antibody techniques. These synthetically produced drugs have shown efficacy and many are in commercial use, but they generally exhibit negative side effects. Clinical improvement can occur with the modulation of individual and/or multiple cytokines.

TNF-α is a cytokine that is involved with systemic inflammation, as well as being key regulator of immune cells. Dysregulation of TNF-α is related to many disease states including inflammatory bowel disease, certain cancers, Alzheimer's disease, inflammatory skin disorders, such as psoriasis and eczema, as well as numerous other conditions. TNF-α antagonist agents have showed that they can mitigate its negative effects. A number of commercial drug products were developed based on being TNF-α antagonists, i.e., Humira®, Enbrel®, Remicade® and others. Further, TNF-α can synergize with interleukin IL-17 to promote inflammation in psoriasis.

IL-1 is an inflammatory cytokine and involved in the immune response. IL-1-alpha receptor antagonist, Anakinra, from Orphan Biovitrum, Sweden, was produced using monoclonal antibody techniques. The molecule is used in a drug to treat rheumatoid arthritis and has shown potential to treat skin diseases, like acne.

Other interleukins include IL-4, for which overproduction is associated with allergies, including airway inflammation in allergic asthma patients. IL-4 and IL-13 are involved in the inflammatory cascade that is involved with atopic dermatitis and allergic asthma. Blockage of IL-4 and IL-13 with their respective receptor antagonists mitigated symptoms in atopic dermatitis and allergic asthma. IL-4 plays a role in chronic inflammation and wound repair. Antagonists of IL-4 receptors help to increase macrophage production, which then reduces pathological inflammation. It helps to activate macrophages that are beneficial to wound healing.

Tissue macrophages play an important role in chronic inflammation and wound repair. The presence of IL-4 in extravascular tissues promotes alternative activation of macrophages into M2 cells and inhibits classical activation of macrophages into M1 cells. An increase in repair macrophages (M2) is coupled with secretion of IL-10 and TGF-β that result in a diminution of pathological inflammation. Release of arginase, proline, polyaminases and TGF-β by the activated M2 cell is tied with wound repair and fibrosis.

IL-4 and IL-13 receptor antagonist, dupilumab (branded as Dupixent), a monoclonal antibody, is provided commercially to treat eczema, and is ingested orally. Reported side effects include allergic reactions, cold sores, dry eye and eye inflammation.

IL-5 is involved with inflammatory diseases including atopic dermatitis. Treatment of severe asthma, sputum eosinophilia and atopic dermatitis with IL-5 antagonists has demonstrated clinical benefits.

IL-6 receptor antagonist, monoclonal antibody tocilizumab was shown to improve symptoms of atopic dermatitis but has the unwanted side effect of promoting bacterial infection—in other words, immune suppression.

IL-12 is an important regulator of both innate and acquired immune response. It is known to stimulate interferon-gamma production, which is involved with resisting bacterial and parasitic infections. It is also involved in antiviral response and in autoimmune diseases. IL-12, in conjunction with IL-18, is involved with the production of IgE and Th2 cytokines, which also play a role in the onset of dermatitis. It is yet further related to the production of numerous inflammatory mediators including IL-1, IL3, IL4, IL-5, IL6, and GM-CSF and TNF-alpha.

TNF-alpha is involved in various inflammatory conditions and its expression was shown to be at elevated levels of TNFR1/TNFR2 in human hepatocellular (HCC) carcinoma patients. HCC is the fifth most common cancer and suppression of TNF-alpha is potentially a part of a therapeutic solution in such situation.

IL-17 is believed to be involved in the immune dysregulation of atopic dermatitis by increasing inflammation. An IL-17 antagonist at its IL17A receptor would be a target to reduce the effect, and reducing inflammation related to atopic dermatitis. For example, secukinumab is based on IL-17A receptor antagonist. Furthermore, IL-17 is involved with inflammatory pathways that affect acne and psoriasis.

IL-22 plays a critical role in the immune system. IL-22 is secreted by a number of different types of lymphocytes. It has been identified as being involved in the pathogenesis of autoimmune diseases, such as psoriasis, rheumatoid arthritis and allergic diseases. It further plays a role in the protective immune response against gram-negative bacteria. Recombinant IL-22 antagonists have been shown to mitigate inflammation and, in this way, may be used to target the aforementioned autoimmune disorders.

Interleukin-31 is involved in the pathogenesis of allergic skin diseases, such as atopic dermatitis, as well as in alopecia, hair loss due to the immune system attacking hair follicles. Further, human monoclonal IL-31 antagonists were shown in studies to decrease itch. For example, in initial clinical studies, the IL-31 monoclonal antibody antagonist, nemolizumab, has shown efficacy in the treatment of atopic dermatitis, with particular improvement in itch. It is an oral formulation.

IL-33 and its IL-33R receptor play a crucial role in atopic dermatitis. In this way, IL-33R antagonists would provide potential clinical benefit for treating this condition. Interferon-gamma is an immune system modulator and stimulator and plays a key role in the immune system's ability to adapt to viral, bacterial or protozoan attack. Expression of interferon-gamma is also linked to numerous autoimmune and inflammatory diseases. For example, it has been shown to play a role in seborrheic dermatitis.

Granulocyte Macrophage—Colony Stimulating Factor (GM-SCF) is an inflammatory mediator. It functions as a cytokine and is involved in protecting the body against infections. GM-CSF levels are high in joints with rheumatoid arthritis. Blocking GM-CSF with an antagonist agent has been shown to reduce inflammation. GM-CSF antagonists are currently in development for clinical use.

Another GPCR of interest is the tachykinin receptor, (TACR1), also called neurokinin 1 receptor (NK1R) or Substance P (SP) receptor. SP is an inducer of nausea and emesis. TAC1 receptor antagonists are used in the prevention of acute and delayed nausea and vomiting, as for patients undergoing cancer chemotherapy or post-surgery nausea. They are taken either orally or injected. Commercial products include Varubi®, Emend®. SP is one of the key initial responders when a body is exposed to stressors and induce the expression of inflammatory cytokines. Cancer is believed to take advantage of TACR and that its antagonists may be useful in cancer treatment. In Phase 2 clinical trials, TACR antagonist Serlopitant has been shown to be effective in treating itch that is associated with atopic dermatitis, psoriasis and prurigo nodularis using a daily, oral application. It is believed that SP is involved in neurogenic inflammation, which is involved in the pathogenesis of psoriasis, eczema, rosacea and other inflammatory conditions. An SP (TACR) antagonist would appear to have significant medicinal value.

HSP90 (Heat Shock Protein 90) is a chaperone protein, with molecular weight of 90 KDa, that facilitates proper protein folding, stabilizes proteins against heat stress, and aids in protein degradation. It also plays a role in signaling for cellular growth and survival pathways. Inhibitors of HSP90 have proven beneficial in cancer treatment, as HSP90 is heavily upregulated by many cancers, enabling tumor cell survival. HsP90 has numerous client proteins and inhibitors have the potential to inhibit many mitogenic pathways, acting as an anti-proliferation agent, namely for tumor cells. Radicicol, also known as monorden, is a HSP90 inhibitor which binds HSP90 and alters its function.

Another class of inhibitors of cell proliferation are called histone deacetylase (HDAC) inhibitors (HDACi). To carry out gene expression, a cell must control the coiling and uncoiling of DNA around "protein spools", called Histones. Histone Deacetylases (HDAC) remove acetyl groups from the DNA backbone, causing that region of the DNA be tightened around the Histone. The tightening silences the region's genes, as they are less accessible for transcription. HDAC6 is a member of the HDAC family which has become a target for drug development to treat cancer due to its major contribution in oncogenic cell transformation. Previous work showed that inhibition of HDAC6 led to tumor cell apoptosis in multiple myeloma. HDAC6 is required for the activation of heat-shock factor 1 (HSF1), an activator of heat-shock protein encoding genes. Further, HDAC6 also affects transcription and translation by regulating HsP90. Valproic acid is one among many of HDACi's.

Valproic Acid has been used for decades in the treatment of epilepsy and recent studies indicate that it could many have anti-cancer effects by increasing responsiveness of tumors to traditional treatments.

BET inhibitors are a class of drugs with anti-cancer, immunosuppressive, and other effects. These molecules reversibly bind the bromodomains of Bromodomain and Extra-Terminal motif (BET) proteins and prevent protein-protein interaction between BET proteins and acetylated histones and transcription factors. BET proteins "read" the positions of protein acetylations which are coordinated in part by HDACs. BET reading is often a prerequisite for protein-histone association and chromatin remodeling. JQ1 is a BET inhibitor of interest for cancer research, because of its ability to inhibit genes which drive such cancers as: NUT midline carcinoma, acute myelogenous leukemia, multiple myeloma, and acute lymphoblastic leukemia. JQ1 has been limited in human clinical trials because of its short half-life.

Modes of Administration

In some embodiments, the methods further comprise the step of washing off the topical formulation from the skin or mucous membrane after a period of time. In certain embodiments, the period of time is under 10, 5, 3, or 1 hour. In other embodiments, the exposure time is under 30, 20, 15, 10, or 5 minutes.

In some embodiments, the methods further comprise daily applications of topical formulations with the therapeutic yeast extract, for a period of between 1 to 4 weeks. In some of these embodiments, the daily application of the topical formulation is followed by the application of a topical corticosteroid formulation (e.g., a cream, lotion, gel or other pharmaceutically acceptable topical formulation) for 2 to 10 days. The corticosteroid includes hydrocortisone, clobetasol propionate, fluocinonide, betamethasone and may include ingested versions. In some embodiments, the sequential application of the topical formulation and corticosteroid is repeated until the symptoms of the disorder ameliorated. The frequency and length of the application cycle for each can vary depending on the individual's specific condition and needs. Both the therapeutic yeast extracts and the corticosteroid could be applied simultaneously or alternating. The regimen of application is flexible and may be adjusted according to the individual needs, and the combined application of corticosteroid and yeast extract displays certain synergistic effects.

In the context of the present disclosure, a "subject" is a mammal, and, particularly, a human. In some embodiments, the subject suffers from a skin disorder, lesion, or growth, with inflammation. In such embodiments, the skin disorder is selected from the group consisting of itch, eczema, atopic dermatitis, seborrheic dermatitis, psoriasis, athlete's foot, acne, dandruff, herpes, hemorrhoids, bug bites, or allergenic plant exposure. In other embodiments, the subject has healthy skin, but the subject desires to help maintain what might be considered a healthy skin condition without inflammation. In some embodiments, these conditions are associated with aging, such as wrinkles, while in other embodiments, the conditions occur in normal individuals, such as dry skin. In some embodiments, the subject has a skin wound and the disclosed methods are used to encourage anti-inflammation and resulting wound healing. In these embodiments, a wound might be a cut, an abrasion, a burn, a tear, bites, or the like, where the wound may be due to an acute insult to the skin, or the wound may be caused by an underlying systemic condition, such as diabetes which manifests as diabetic skin ulcers, namely on the feet, as an example, or where the wound is caused by repeated mechanical, chemical, or environmental exposure or a combination thereof. Levels of inflammatory cytokines, such as IL-8 and TNF-alpha are increased in patients with diabetic foot ulcers. Levels of IL-1 and GM-CSF serum levels are reduced with complete wound healing. Conversely, inflammatory markers such as IL1 and TNFα were reported to be at significantly higher levels in chronic venous ulcers than in normally healing wounds.

The term "treat," "treating," "treatment," or any other variation thereof, does not indicate the complete cure of a disorder. Any amelioration or alleviation of the inflammation and symptoms of a diseases or disorder to any degree, or any increase in the comfort of the subject, is considered treatment.

Production of yeast extracts of the current invention is a further development of the methods previously disclosed in U.S. Pat. Nos. 7,476,529, 7,645,730, 7,659,237 and 7,759,301 which are here incorporated in their entirety. The art in these inventions is, by their definition, necessarily a combination of the yeast extract with a surfactant. The current invention found that the processes, as defined, provide a therapeutic yeast extract, which in and of itself, displays the therapeutic effects and features that are noted herein without a surfactant. In some embodiments a surfactant may be added to a formulation to improve wetting or, for example, in a therapeutic wash formulation, by necessity as a stand-alone feature and not synergizing with the extract materials. In one embodiment the fermentation can be done under either anaerobic, or aerobic conditions, or combinations thereof. Another embodiment of the production of the therapeutic yeast extracts includes disruption, or lysis of the yeast cells, to release the intracellular materials. In a further embodiment, the intracellular cell materials are spilled without the use of an enzyme. In another embodiment, the disruption of the yeast cell wall is done without a surfactant. The soluble materials are isolated, preferably by centrifugation, from the insoluble materials, and the liquid is retained. Disruption of the cells is not a limiting feature, as techniques are well known to those skilled in the art, and include mechanical disruption, homogenization, ultrasound, freeze/thaw cycles, temperature, irradiation, certain chemical additions, that can be adjusted optimally to release the intracellular materials.

When treating sensitive skin conditions, it is important to remove any potentially antagonistic materials, a feature that has not been addressed in other yeast extracts. This extra step(s) in the process adds costs, which can affect commercial viability of an extract, but is seen as a necessary addition for many uses described herein. In contrast to this embodiment, in many instances yeast extracts are marketed such that their minerals and other constituents are beneficial by providing nutrients etc., to the skin being treated Thus, in a preferred embodiment of the current invention, a substantial amount of undesirable residue is removed, and constituents that are anti-inflammatory and uncoupling agents that are active in animal, preferably mammalian, and most preferably human, cells that are produced are substantially retained. This can be achieved by any one of a number of techniques known to those skilled in the art, such as adjusting the fermentation parameters, and with filtration, ion exchange, molecular sieves or other appropriate method. For the purposes of the current invention, undesirable residue can include the following, non-limiting examples: yeast cell wall materials, breakdown products from the fermentation, excess chemicals that are not taken up by the yeast during propagation, any added chemicals, and which may be removed or optionally neutralized and insoluble materials. The degree to which residue is removed is optional as cost and yield considerations may affect the process(es) chosen and the feature is a non-limiting feature of the current invention, and the undesirable materials may be different for different uses and application methods. Undesirable residue may further include those that interfere with the therapeutic yeast extract signaling antagonist agent constituents. In a further embodiment, the process eliminates a substantial amount of undesirable constituents that are above about 4 kDa in molecular weight using techniques known to those skilled in the art, such as filtration, ion exchange, molecular sieves or combinations, or other appropriate method until the desired level of purification for a particular affliction and appropriate for the method of application is achieved.

One embodiment of the current invention comprises a step to apply non-lethal stress to the yeast prior to extraction, before, during or after the fermentation steps. Applied stress may be of physical (temperature, sonication, radiation) or chemical (such as, but not limited to hydrogen peroxide exposure), etc. After fermentation and stress, the yeast cells are disrupted by methods known to those skilled in the art that include mechanical, thermal, or other means of yeast cell disintegration, or combinations thereof. It is an established fact that different forms of stress induce the same stress proteins and the stressing agents used are not a limiting factor of the current invention.

The parameters defined in the current patent afford a range of conditions and it is important to specify such conditions that necessarily produce therapeutic yeast extracts that contain the anti-inflammatory or inflammation regulating agent, anti-itch agents, which include histamine receptor antagonists and/or inflammatory cytokine receptor antagonists, and uncoupling agents that are active in animal, preferably mammalian, and most preferably human, cells.

We have discovered that such yeast extracts assist in the treatment, healing, and relief of inflammatory conditions, such as, but not limited to, skin lesions, itch, psoriasis and eczema (atopic dermatitis), acne, herpes, dandruff/seborrheic dermatitis, hemorrhoids, athlete's foot, growths, tumors, in addition to improvement in wound/burn healing, fibrosis, and scarring.

In some embodiments, in the compositions disclosed herein for skin treatments, the therapeutic yeast extract demonstrates its benefits being applied on its own, however preferably, at a minimum, a preservative is added for long-term storage. Preservative choice is not a limiting feature of the current invention. The preservatives can be chosen from typical cosmetic ones that includes, but are not limiting, parabens, formaldehyde releasers, isothiazolinones, phenoxyethanol, organic acids and their salts, as well as certain herbal extracts, such as grapefruit seed extract and others. The compositions may comprise no surfactant, where its addition may be antagonistic to sensitive or inflamed skin. In other embodiments, one or more surfactant, or other ingredients typically used in skin care are included, for example as in a wash solution that has therapeutic properties, and at a wide range of concentration levels targeted to specific end uses. Those surfactants may be synthetic, or, preferably, bio-based, such as alkyl polyglucosides, or phospholipids.

In another embodiment, the compositions of the current invention may further include ingredients taken from the following list of non-limiting examples: (a) anti-inflammatory agents that include, vitamin E, coenzyme Q10, hyaluronic acid, salicylic acid, corticosteroid, dimethicone, curcuminoids (anti-inflammatory) cannabinoids; (b) anti-itch agents that include, witch hazel, oatmeal, D-panthenol (ProVitamin B5), camphor, calamine; (c) other ingredients, such as, petroleum jelly, ceramide, cocoa butter, lanolin, shark liver oil, an antifungal agent, peroxides, benzoyl peroxide, anti-microbial agents, thickening agents, retinoids, hydroquinone as a skin lightener, coconut oil.

In some embodiments, the compositions with the therapeutic yeast extract are formulated as a liquid, gel, oil, lotion, cream or other appropriate topical medium.

Throughout the present disclosure the term "about" a certain value means that a range of value±10%, and preferably a range of value±5%, is contemplated. Thus, for example, having about 70% of an ingredient or constituent includes it being present between 63% and 87%, and preferably between 66.5% and 73.5%.

The concentration of the yeast derived extract in the finished product may depend on the concentration of the extract, which, in turn, may vary depending on the concentration of yeast suspension at the fermentation and post-fermentation steps. In one non-limiting example presented here, the total non-volatile dissolved solids (NVS) in the therapeutic yeast extract that was used in tests, was under 3% and where at least 90%, preferably 98% of the NVS being the proteinaceous material (sum of proteins, peptides and amino acids and co-factors). Details can be adjusted to specific performance, purity and cost needs for particular end uses. The values are presented as a reference.

It was found that the therapeutic yeast extracts disclosed herein, when applied without any added ingredients, such as hydrating agents, on skin areas affected by psoriasis, or eczema, improved the skin condition quite dramatically, and, in most instances, relief of itch was immediate, within a couple minutes or, in more severe cases, within 15 to 30 minutes. In a key embodiment, the therapeutic yeast extract comprises histamine receptor antagonist agents for each of the 4 histamine receptors, H1R, H2R, H3R and H4R. The therapeutic yeast extract was found to be a potent competitive antagonist of HxRs. This is demonstrated by the dramatic increases in the IC50 (the concentration at which the antagonist exerts 50% of its effect) in the presence of the extract, relative to control. The maximum response of HxRs is unaffected, suggesting that the therapeutic yeast extract acts as a competitive inhibitor of agonist binding. The therapeutic yeast extract antagonizes both H1R and H4R, the most significant of the HxRs. Competitive inhibition is not seen in either commercial yeast extracts (dehydrated or hydrated). The increased Hill coefficients with the introduction of the therapeutic yeast extracts point towards their ability to enhance cooperative binding in Antagonists. This could be due to the HxRs recruitment of Dopamine receptors.

In another embodiment, the therapeutic yeast extracts comprise Substance P receptor antagonists. The therapeutic yeast extract is a potent, competitive antagonist to TACR1. This is evidenced by the dramatic increase in RC50 of TACR1 agonists in the presence of the therapeutic yeasty extract. Significantly, the antagonistic effect of the extract is corroborated in both the Arrestin and Calcium Flux assays. This indicates that endogenous pathway response is consistent with the response of the TACR1 receptor. In some cases, endogenous activity modulates receptor response and a lack of consistency is seen with the bound receptor and the activated pathways. Here, this is not the case. Nominal increases in the Max Response are also observed, likely due to the increased cooperativity affected by the therapeutic yeast extract.

In another embodiment, the therapeutic yeast extract comprises inflammatory cytokine receptor antagonists, which are believed to help control dysregulated inflammatory cytokine expression. This is not a limiting factor in the current invention and noted as a possible mechanism. These include, but are not limited to, the following, or their combinations: TNF-alpha, GM-CSF, Interfero-gamma, IL-1, IL-2, IL-4, IL-5, IL-6, IL-12, IL-13, IL-17, IL-22, IL-31, IL-33. The therapeutic yeast extract exhibits a particularly strong effect as a competitive antagonist for IL17RD/TNFR2, IL1R1/IL1RAP, IL3RA/OSMRb, & IL4R/L2RG. Antagonism most significantly affected IL3RA/OSMRb, and IL4R/L2RG. Antagonism increased the efficacy (evidenced by higher Max Responses) at very high concentrations. The increased Hill coefficients with the introduction of the therapeutic yeast extracts point towards their ability to enhance cooperative binding in Antagonists.

In some embodiments, the therapeutic yeast extracts act as an anti-inflammatory agent. In another embodiment, the therapeutic yeast extract comprises an anti-itch agent. In other embodiments, the therapeutic yeast extracts are not subjected to any chemical treatment after the disruption of yeast cells for use in skin treatment. In some embodiments, the therapeutic yeast extract is exposed to acid addition. The therapeutic yeast extract was further found to be a mild uncoupling agent of eukaryotic cells, with in vitro tests performed on adult skin fibroblasts. Uncoupling agents, as used in the current invention, refer to those that uncouple oxidative phosphorylation in animal, preferably mammalian, and most preferably human, cells. Uncoupling agents are agents that disrupt the connection between oxidation of nutrients and synthesis of adenosine triphosphate (ATP). In mitochondria of animal, preferably mammalian, and most preferably human, cells, oxidation of nutrients leads to transfer of protons across the inner mitochondrial membrane resulting in the formation of the trans-membrane proton gradient. Proton gradient then activates ATP-synthase complex imbedded in mitochondrial membrane. When protons move back across the membrane thru the ATP-synthase proton channel, ATP is formed out of ADP and phosphate. ATP is then used as a universal source of energy for all energy-consuming processes in the cell. In coupled mitochondria, the rate of oxidation is limited by the rate of ATP utilization (phosphorylation control). Uncouplers facilitate the proton leak across the membrane thus quenching proton gradient and preventing ATP formation. Lifting phosphorylation control results in accelerated oxidation, i.e. enhanced oxygen consumption. Uncoupling is intimately related to the production of reactive oxygen species (ROS) and thus to inflammations, immune response, infection control, etc. Standard chemical uncouplers, e.g., 2,4-dinitrophenol (DNP), or Carbonyl cyanide-4-(trifluoromethoxy)phenylhydrazone (FCCP), are all toxic chemicals. Cells also produce uncoupling proteins (UCP) which are imbedded into inner mitochondrial membrane. UCPs form trans-membrane proton leak channels and this way contribute to respiration control. Further, uncouplers have been shown to inhibit TNF induced inflammation in endothelial cells and TNF-induced endothelial lethality. In a further embodiment, the therapeutic yeast extract comprises one or more uncoupling agents that are active in animal, preferably mammalian, and most preferably human, cells, as revealed by oxygen consumption increase in a bulk cell culture of adult skin fibroblasts.

In another embodiment, the therapeutic yeast extracts act as a cell proliferation inhibitor agent. Cell anti-proliferation is either individual affect upon, or a combination of effects as an HsP90 inhibitor agent, HDAC inhibitor agent and/or BET inhibitor agent.

The following is a list of preferred embodiments:

Embodiment 1

A composition comprising a therapeutic extract from yeast that comprises:

(a) an anti-inflammatory agent; and (b) an uncoupling agent active in animal, preferably mammalian, and most preferably human, cells.

Embodiment 2

The composition of embodiment 1 where the anti-inflammatory agent is an anti-itch agent.

Embodiment 3

The compositions of embodiments 1 and 2, wherein the anti-inflammatory agent, or the anti-itch agent is a histamine receptor antagonist agent.

Embodiment 4

The composition of one of embodiments 1-3, wherein the anti-inflammatory agent or the anti-itch agent comprises one or both of a GPCR antagonist agent and a cytokine receptor antagonist agent.

Embodiment 5

The composition of one of embodiments 1-4, wherein the anti-inflammatory agent comprises one or more of an HSP90 inhibitor agent, a HDAC inhibitor agent and a BET inhibitor agent.

Embodiment 6

The composition of one of embodiments 1-5, wherein the composition is antiproliferative to one or more of human primary B cells, endothelial cells, fibroblasts, and coronary artery smooth muscle cells in an in vitro cell based proliferation assay.

Embodiment 7

The composition of one of embodiments 4-6, wherein at least about 98% of the cytokine receptor antagonist agent present in the composition, and optionally one or both of the GPCR antagonist agent and the uncoupling agent, is under a molecular weight of about 4,000 daltons.

Embodiment 8

The composition of embodiment 7, wherein at least about 90% the cytokine receptor antagonist agent, and optionally one or both of the GPCR antagonist agent and the uncoupling agent, present in the composition is soluble.

Embodiment 9

The composition of one of embodiments 1-8, wherein the extract is a *Saccharomyces ceverisiae* extract.

Embodiment 10

The composition of one of embodiments 1 to 9, wherein the therapeutic yeast extract comprises soluble constituents, is substantially colorless and odorless, and is devoid of insoluble materials that may be separated from soluble matter, preferably by centrifugation.

Embodiment 11

The compositions of one of embodiments 1-10, wherein the therapeutic yeast extract is substantially free of undesirable residue.

Embodiment 12

The composition of one of embodiments 3-11, wherein the histamine receptor antagonist is an antagonist for one or more of H1R, H2R, H3R and H4R histamine receptors.

Embodiment 13

The composition of one of embodiments 4-12, wherein the cytokine receptor antagonist agent is an antagonist for a receptor of a cytokine selected from the group consisting of TNF-alpha, interferon-gamma, Granulocyte-macrophage colony-stimulating factor (GM-CSF), IL-1, IL-2, IL-4, IL-5, IL-6, IL-12, IL-13, IL-17, IL-22, IL-31, IL-33.

Embodiment 14

The composition of one of embodiments 4-13, wherein the GPCR antagonist agent is a Substance P receptor antagonist agent.

Embodiment 15

The composition of one of embodiments 4-14, wherein the GPCR antagonist agent, the cytokine receptor antagonist agent, and the uncoupling agent are soluble in the composition, and wherein about 98% of the GPCR antagonist agent, the cytokine receptor antagonist agent, and the uncoupling agent are under a molecular weight of about 4,000 daltons.

Embodiment 16

The composition of one of embodiments 1-15 that further comprises: a preservative, an antimicrobial agent, an emollient, a fragrance, or combinations thereof.

Embodiment 17

A method of obtaining a therapeutic yeast extract of one of embodiments 1-16, comprising:

Embodiment 17

A method of obtaining a therapeutic yeast extract of one of embodiments 1-16, comprising:
(a) fermenting yeast, wherein the fermenting step comprises more than one fermentation procedure, and wherein the fermenting step optionally comprises one or both of the following steps the fermenting step optionally comprises at least one fermentation procedure under anaerobic conditions, and
    the fermenting step optionally comprises at least one fermentation procedure at a temperature greater than 30° C.;
(b) subjecting the yeast to a stress;
(c) disrupting or lysing the yeast;
(d) purifying the yeast to substantially remove undesirable residue; and
(e) separating insoluble material from the liquid soluble materials.

Embodiment 18

A method according to embodiment 17, wherein the fermenting step comprises a total fermentation time of between 1 hour and to about 2 weeks.

Embodiment 19

A method of treating a subject in need of an anti-itch medication, comprising: administering a composition according to one of embodiments 1-16 to the subject, wherein the subject is in need of the anti-itch medication due to the presence of eczema, psoriasis, atopic dermatitis, acne, dandruff, hemorrhoids, herpes, dry eye, eye allergies, or other inflammatory condition.

Embodiment 20

A method of treating a subject in need of reducing an inflammatory condition due to the presence of eczema, psoriasis, atopic dermatitis, acne, dandruff, hemorrhoids, herpes, dry eye, eye allergies, or other inflammatory condition: administering a composition according to one of embodiments 1-16 to the subject.

Embodiment 21

A method treating a subject in need of skin improvement, comprising administering a composition according to one of embodiments 1-16 to the subject.

Embodiment 22

A method according to one of embodiments 19-21, wherein the administration is topical.

EXAMPLES

Example 1. Histamine Receptor Antagonist Tests

An in vitro assay was used to determine the activity of the therapeutic yeast extract on the effects on the 4 GPCR receptors, the histamine receptor sites, H1R, H2R, H3R and H4R. DiscoverX Corporation, PathHunter® β-Arrestin assay was used. It monitors the activation of a GPCR in a homogeneous, non-imaging assay format. The test used reagents that were focused on the histamine GPCR's. A dose response was studied, where the therapeutic yeast extract was diluted from 16%, with 10 data points, with a diluting factor of half per data point. Results of IC50 in Table 1, measured in percent (%) v/v of therapeutic yeast extract. IC50 is the concentration of the receptor antagonist where the response (or binding) is reduced by half. EC50 is the concentration of a drug that gives half of the maximum response.

Histamine is a strong itch inducer. H1R and H4R, especially H4R, are of most interest with regard to being targets for mitigating both short term and chronic itch-related skin afflictions. The result for H4R, known to play a role in itch, at 4.74%, which incidentally is in the range of the concentration of the therapeutic yeast extract used in the test formulation. The therapeutic yeast extracts are a potent competitive antagonist of HxRs. This is demonstrated by the dramatically low IC50% s in the presence of therapeutic yeast extracts, relative to control. Therapeutic yeast extracts antagonize both H1R and H4R, the most significant of the HxRs for itch response. The increased Hill coefficients at high concentrations of therapeutic yeast extracts point towards its ability to enhance cooperative binding in Histamine past a threshold concentration. This is indicated by the simultaneous and step-wise binding displayed by Histamine to HxRs. This could be due to therapeutic yeast extracts coordinating the recruitment of HxRs which then act heterodimerically. The role of therapeutic yeast extracts recruiting multiple receptors for cooperative binding is supported by its results in Cytokine Receptors, which are known to be heterodimeric. Increased cooperativity could also explain the nominal increase in the max response of HxRs in the presence of the therapeutic yeast extracts at high agonist concentrations. These results and conclusions are non-limiting for the purposes of the patent and are provided as a possible mechanism that supports the claims being made.

TABLE 1

Summary of HxR Antagonist Study for Therapeutic Yeast Extract.

| Assay Target | IC50 (%) | Hill | Curve Bottom | Curve Top | Max Response |
|---|---|---|---|---|---|
| HRH1 | 9.578864 | 5.745 | −28.383 | 120 | 114.44 |
| HRH2 | 4.128127 | 1.9074 | −6.4895 | 128.97 | 118.35 |
| HRH3 | 6.827442 | 2.3727 | −5.5866 | 100 | 127.29 |
| HRH4 | 4.746167 | 3.4629 | −12.751 | 100 | 84.81 |

Example 2. Substance P, TACR1 Antagonist Assay on Therapeutic Yeast Extracts TACR1 antagonist assay was performed using PathHunter® β-Arrestin assay and the Calcium No WashPLUS assay. Results were consistent with the therapeutic yeast extract data for histamine and cytokine receptor antagonists assays, and efficacy was found to be in the range of commercial use. Results are shown in Table 11. The therapeutic yeast extracts are a potent, competitive antagonist to Substance P receptor, TACR1. This is evidenced by the dramatically low IC50% of Substance P in the presence of the extract. Significantly, the antagonistic effect of the therapeutic extracts is corroborated in both the Arrestin and Calcium Flux assays. This indicates that endogenous pathway response is consistent with the response of the TACR1 receptor. In some cases, endogenous activity modulates receptor response and a lack of consistency is seen with the bound receptor and the activated pathways. Here, this is not the case. Nominal increases in the Max Response are also observed, likely due to the increased cooperativity affected by the therapeutic yeast extracts. The increased Hill coefficients point to enhanced cooperative binding at high concentrations of the yeast extracts.

TABLE 2

Summary of Substance P, TACR Antagonist Assay for Therapeutic Yeast Extract

| Assay Target | IC50 (%) | Hill | Curve Bottom | Curve Top | Max Response |
|---|---|---|---|---|---|
| TACR1 | 6.52735 | 2.463 | 4.5541 | 115 | 107.75 |
| TACR1 | 1.04914 | 1.3715 | 3 | 112.33 | 104.56 |

Example 3. Comparing IC50 Commercial Yeast Extracts for HxR Antagonist Activity Two commercial yeast extracts, Sample A and Sample B, were tested for HxR antagonist potential, Sample A and Sample B. Sample A is from Biospringer, Inc.—Springer® 1405/40-MG-L is a spray-dried yeast extract of *Saccharomyces cerevisiae*, grown on a molasses-based media. Sample B is a liquid yeast extract from Advanced BioCatalytics Corp. that is used in its Accell® product. The IC50 results are shown in Table 12. Values >16 do not exhibit an antagonist effect. Human tests of Sample B showed that it increased the itch sensation in a subject with broken skin that was due to plaque psoriasis, though it had about half of the histamine levels than the therapeutic yeast extract. As a side note, when generating the raw data for Samples A and B, the results were difficult to read, which is a sign of interference of certain materials in those samples, and data further indicated that the cell cultures might have been killed off at the higher concentrations, suggesting incompatibility of both Sample A and B for the intended uses. The results on the therapeutic yeast extracts were more easily obtained and showed solid curves. Competitive inhibition is not seen in either commercial yeast extract tested (dehydrated or liquid).

TABLE 3

HxR Antagonist comparison of commercial yeast extracts in antagonist mode, IC50 measured as % of sample.

| Assay Name | Result Type | H1R | H2R | H3R | H4R | Histamine Level |
|---|---|---|---|---|---|---|
| Sample A | Arrestin IC50 (%) | >16 | >16 | 6.5 | >16 | — |
| Sample B | Arrestin IC50 (%) | >16 | >16 | >16 | >16 | 1.11 ppm |
| Therapeutic Yeast Extract | Arrestin IC50 (%) | 9.6 | 4.1 | 6.8 | 4.7 | 0.64 ppm |

Comparative tests were run on commercial yeast extracts, Sample A and B in both antagonist and agonist mode. Results shown in Tables 13 and 14 indicate that the commercial yeast extracts do not have any significant level of binding to the Histamine or Substance P receptor sites. And this suggests that these extracts do not have the therapeutic effects that are seen by the therapeutic yeast extract of the current invention.

TABLE 4

Substance P (TACR1) receptor antagonist comparison of commercial yeast extracts in antagonist mode.

| Assay Name | Assay Target | Material | $EC_{50}$ (%) | Max Response |
|---|---|---|---|---|
| Ca Flux | TACR1 | Sample A | >20 | 27.5 |
| Ca Flux | TACR1 | Sample B | >20 | 6.1 |

TABLE 5

Calcium Flux Assay, comparison of commercial yeast extract in agonist mode.

| Assay Name | Assay Target | Material | $EC_{50}$ (%) | Max Response |
|---|---|---|---|---|
| Ca Flux | H1R | Sample A | >20 | 6.1 |
| Arrestin | H4R | Sample A | >20 | 27.5 |
| Ca Flux | H1R | Sample B | >20 | 11.6 |
| Arrestin | H4R | Sample B | >20 | 14.0 |

Example 4. Cytokine Receptor Antagonist Tests

An in vitro assay, by DiscoverX Corporation, PathHunter® Cytokine Receptor Assay was used to generate the results. The results are in Table 15. The therapeutic yeast extracts are a potent antagonist of numerous key receptors in the inflammatory cascade. The results indicate that the therapeutic yeast extracts have a notable dose response, as it is clear from the IC50(%) column for all cytokines listed, supporting the performance seen in human use studies, where efficacy is shown in a broad range of inflammatory conditions that is hypothesized to be, at least in part, due to the action on the receptors. Antagonism increases the efficacy (evidenced by higher Max Responses) at very high concentrations. The increased Hill coefficients points toward enhanced cooperative binding in agonists. It is hypothesized, but limiting to the current invention, that by blocking the inflammatory cytokines, the therapeutic yeast extracts of the current invention act to mitigate a wide range of inflammatory conditions.

Additional support corroborating the action of the therapeutic yeast extracts as a IL-1 receptor antagonist was found in the BioMAP phenotype profiling results. The therapeutic yeast extracts and Anakinra share 8 common activities in systems modeling: (a) vascular inflammation regulation in venular endothelial cells and coronary artery smooth muscle cells, and (b) immune activation in peripheral blood mononuclear cells and B cells, a lymphocyte that produces antibodies. Anakinra is a recombinant IL-1 receptor antagonist (IL-1RA) that blocks the binding of naturally-occurring IL-1 to the IL-1 receptor and is approved for the treatment of rheumatoid arthritis.

TABLE 6

Summary of Cytokine Antagonist Study, therapeutic yeast extracts.

| Compound Name | Assay Target | IC50 (%) | Hill | Curve Bottom | Curve Top | Max Response |
|---|---|---|---|---|---|---|
| TNF-α | IL17RD/TNFR2 | 3.84877 | 1.2805 | −0.95198 | 170 | 152.37 |
| GM-CSF | CSF2RB/CSF2RA | 4.72028 | 1.9834 | −0.52144 | 130 | 125.91 |
| Interferon-γ | IFNGR1/IFNGR2 | 10.0860 | 1.8909 | 3.0787 | 130 | 109.28 |
| IL-1 α | IL1R1/IL1RAP | 3.55490 | 2.2375 | 0.6762 | 130 | 127.42 |
| IL-2 | IL2RB/IL2RG/IL2RA | 6.98687 | 4.2413 | −5.3386 | 115 | 107.28 |
| IL-4 | IL4R/IL2RG | 7.21792 | 2.8264 | −1.3325 | 150 | 131.09 |
| Il-5 | IL5RA/CD131 | 6.26383 | 1.9167 | −0.921 | 130 | 120.19 |
| IL-6 | Il6R/IL6ST | 4.92270 | 1.5329 | 1.4016 | 120 | 108.92 |
| IL-12 | IL12RB/IL12RB2 | 4.4566 | 1.3039 | 7.1503 | 150 | 133.35 |

TABLE 6-continued

Summary of Cytokine Antagonist Study, therapeutic yeast extracts.

| Compound Name | Assay Target | IC50 (%) | Hill | Curve Bottom | Curve Top | Max Response |
|---|---|---|---|---|---|---|
| IL-13 | IL4R/IL13RA1 | 7.00397 | 2.2461 | 7.3985 | 210 | 193.16 |
| IL-17A | Il17A/IL17RC | 5.95102 | 4.8786 | 4.1422 | 125 | 121.44 |
| IL-22 | IL22RZ/IL10RB | 6.54724 | 1.2165 | 2.7664 | 130 | 115.26 |
| IL-31 | IL31RA/OSMRb | 5.86165 | 1.9642 | 5.2193 | 115 | 106.84 |
| IL-33 | IL1R1/IL1RAP | 2.00226 | 1.275 | 10 | 119.8 | 110.28 |

Example 5. Mechanism-of-Action Classification Based on Phenotypic Assays

In this study, the therapeutic yeast extracts were characterized by phenotype profiling in the BioMAP Diversity PLUS panel of human primary cell-based assays modeling complex tissue and disease biology of organs. See, e.g., Berg et al., J. Biomol. Screening 18: 1260-69, 2013. BioMAP panels consist of human primary cell-based systems designed to model different aspects of the human body in an in vitro format. The 12 systems in the Diversity PLUS panel allow test agent characterization in an unbiased way across a broad set of systems modeling various human disease states. BioMAP systems are constructed with one or more primary cell types from healthy human donors, with stimuli (such as cytokines or growth factors) added to capture relevant signaling networks that naturally occur in human tissue or pathological conditions. Vascular biology is modeled in both a Th1 (3C system) and a Th2 (4H system) inflammatory environment, as well as in a Th1 inflammatory state specific to arterial smooth muscle cells (CASM3C system). Additional systems recapitulate aspects of the systemic immune response including monocyte-driven Th1 inflammation (LPS system) or T cell stimulation (SAg system), chronic Th1 inflammation driven by macrophage activation (1 Mphg system) and the T cell-dependent activation of B cells that occurs in germinal centers (BT system). The BE3C system (Th1) and the BF4T system (Th2) represent airway inflammation of the lung, while the MyoF system models myofibroblast-lung tissue remodeling. Lastly, skin biology is addressed in the KF3CT system modeling Th1 cutaneous inflammation and the HDF3CGF system modeling wound healing.

Cell types and stimuli used in each system are as follows: 3C system [HUVEC+(IL-1β, TNFα and IFNγ)], 4H system [HUVEC+(IL-4 and histamine)], LPS system [PBMC and HUVEC+LPS (TLR4 ligand)], SAg system [PBMC and HUVEC+TCR ligands], BT system [CD19+ B cells and PBMC+(α-IgM and TCR ligands)], BF4T system [bronchial epithelial cells and HDFn+(TNFα and IL-4)], BE3C system [bronchial epithelial cells+(IL-1β, TNFα and IFNγ)], CASM3C system [coronary artery smooth muscle cells+(IL-1β, TNFα and IFNγ)], HDF3CGF system [HDFn+(IL-1β, TNFα, IFNγ, EGF, bFGF and PDGF-BB)], KF3CT system [keratinocytes and HDFn+(IL-1β, TNFα, IFNγ and TGFβ)], MyoF system [differentiated lung myofibroblasts+(TNFα and TGFβ)](and 1 Mphg system [HUVEC and M1 macrophages+Zymosan (TLR2 ligand)]. Systems are derived from either single cell types or co-culture systems. Adherent cell types are cultured in 96 or 384-well plates until confluence, followed by the addition of PBMC (SAg and LPS systems). The BT system consists of CD19+ B cells co-cultured with PBMC and stimulated with a BCR activator and low levels of TCR stimulation.

The yeast extract composition was added at the indicated concentrations 1-hr before stimulation and remained in culture for 24-hrs or as otherwise indicated (48-hrs, MyoF system; 72-hrs, BT system (soluble readouts); 168-hrs, BT system (secreted IgG)). Each plate contained drug controls (e.g., legacy control test agent colchicine at 1.1 μM), negative controls (e.g., non-stimulated conditions) and vehicle controls (e.g., 0.1% DMSO) appropriate for each system. Direct ELISA was used to measure biomarker levels of cell-associated and cell membrane targets. Soluble factors from supernatants were quantified using either HTRF® detection, bead-based multiplex immunoassay or capture ELISA. Overt adverse effects of test agents on cell proliferation and viability (cytotoxicity) were detected by sulforhodamine B (SRB) staining, for adherent cells, and alamarBlue® reduction for cells in suspension. For proliferation assays, individual cell types were cultured at subconfluence and measured at time points optimized for each system (48-hrs: 3C and CASM3C systems; 72-hrs: BT and HDF3CGF systems; 96-hrs: SAg system). Cytotoxicity for adherent cells was measured by SRB (24-hrs: 3C, 4H, LPS, SAg, BF4T, BE3C, CASM3C, HDF3CGF, KF3CT, and/Mphg systems; 48-hrs: MyoF system), and by alamarBlue staining for cells in suspension (24-hrs: SAg system; 42-hrs: BT system) at the time points indicated.

Figure 3:
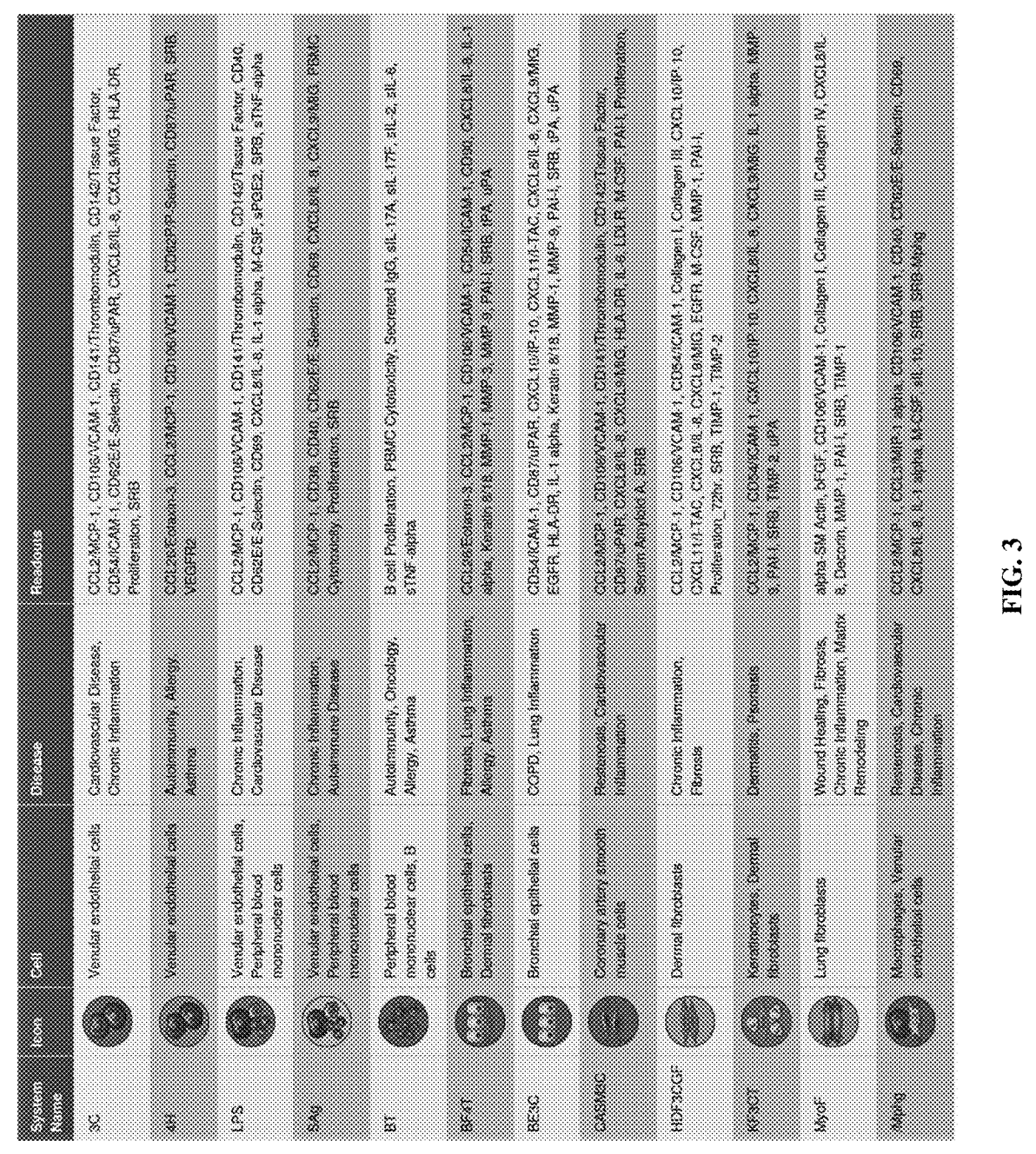

Each test agent generates a signature BioMAP profile that is created from the changes in protein biomarker readouts within individual system environments. Biomarker readouts (7-17 per system) are selected for therapeutic and biological relevance, are predictive for disease outcomes or specific drug effects and are validated using agents with known mechanism of action (MoA). In total, the Diversity PLUS panel contains 148 biomarker readouts that capture biological changes that occur within the physiological context of the particular BioMAP system. The Biomarkers in each system are depicted in FIG. 3.

The BioMAP profile pooled previous data to make a similarity assessment between the therapeutic yeast extracts and other biologics. Similarity was quantified by a Pearson's correlation coefficient, where a coefficient greater than 0.7 indicates a high degree of similarity in mechanism of action.

Figure 1B:
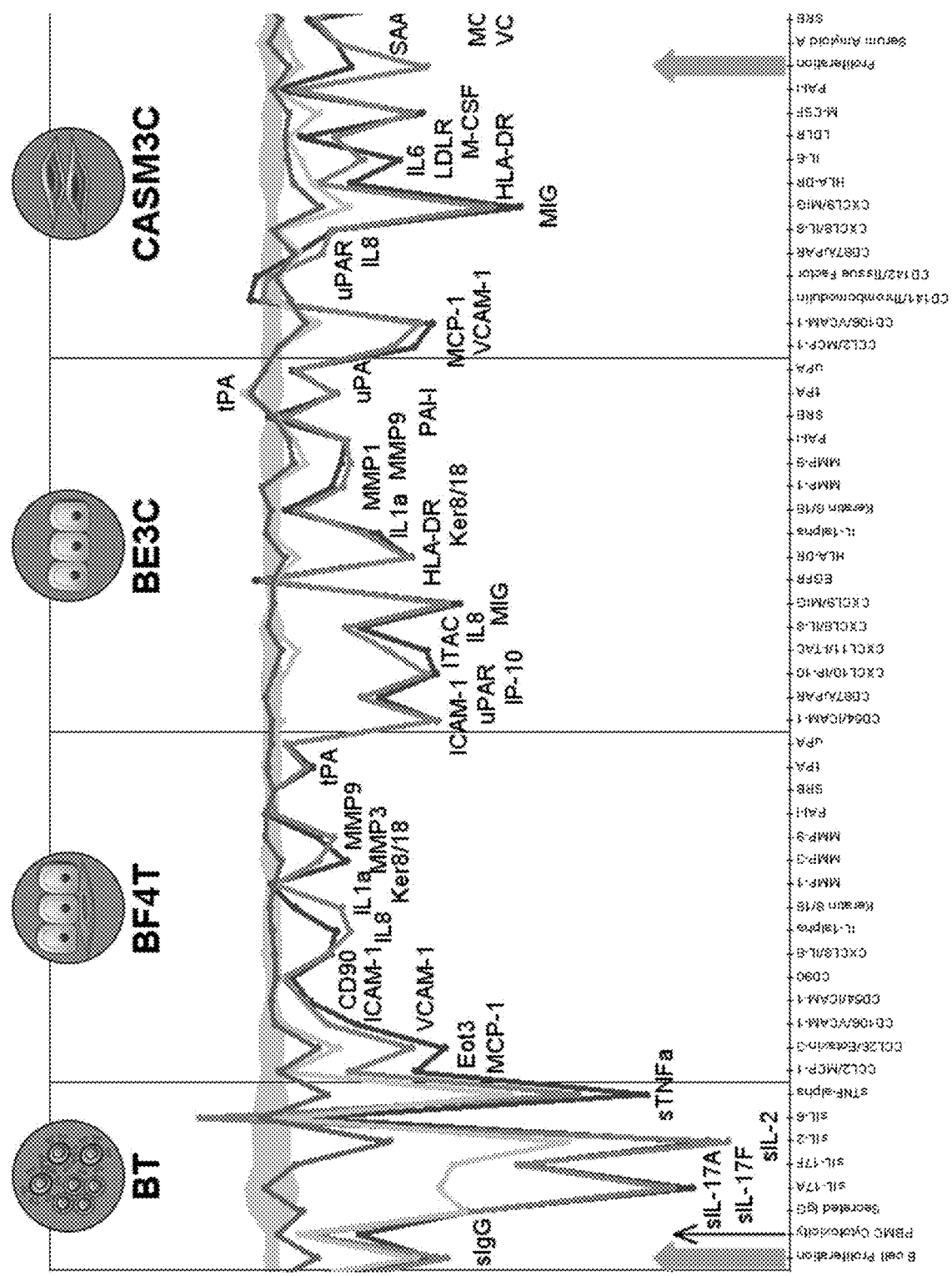
FIG. 1B depicts the results of phenotype profiling of a yeast extract composition of the present invention in the BioMAP Diversity PLUS panel 3C, 4H, LPS and sAg systems.
Figure 1C:
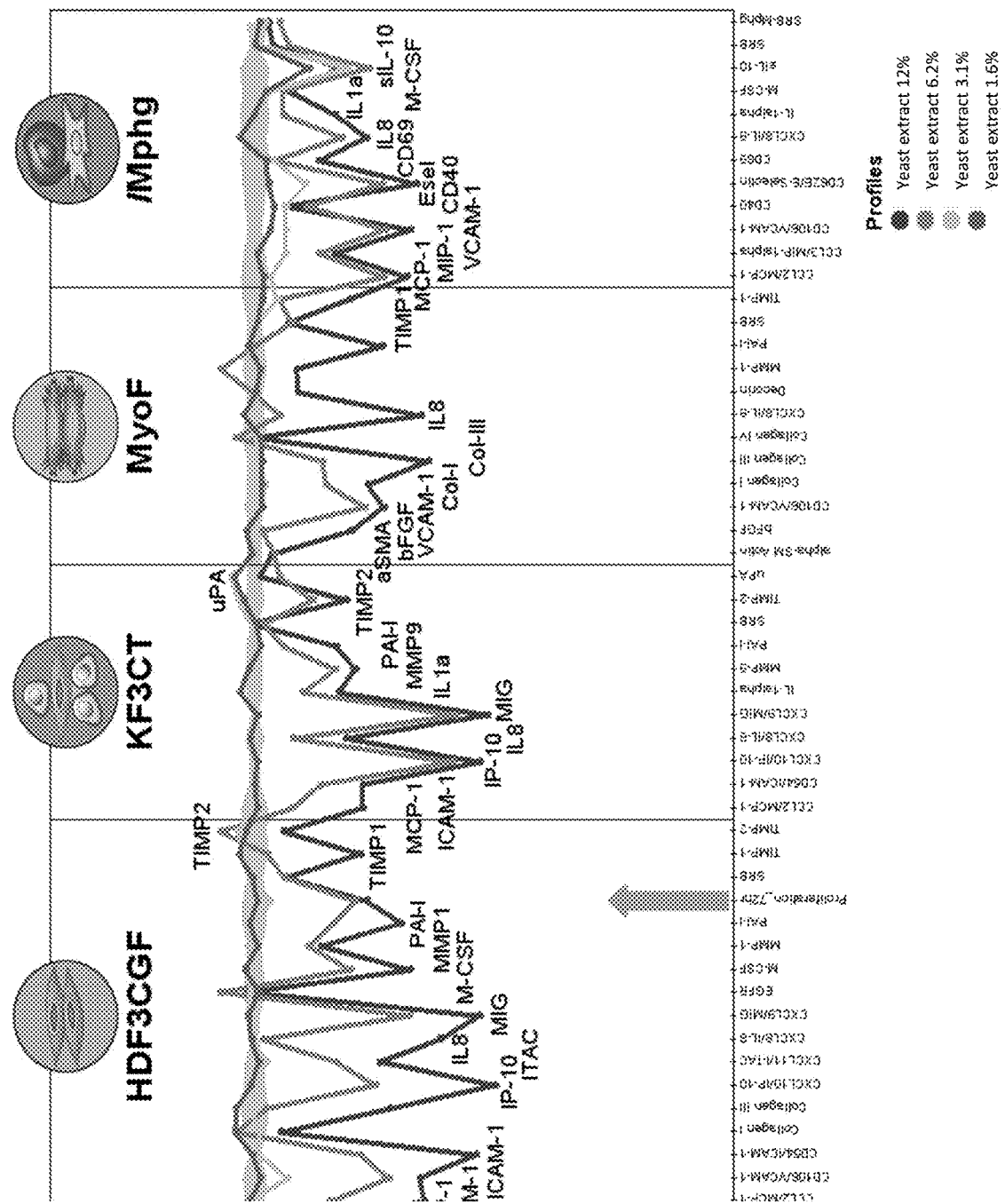
FIG. 1C depicts the results of phenotype profiling of a yeast extract composition of the present invention in the BioMAP Diversity PLUS panel HDF3CGF, KF3CT, MyoF, and/Mphg systems.

The BioMAP profile of a yeast extract composition of the present invention is shown in FIGS. 1A-C. In each figure, the X-axis lists the quantitative protein-based biomarker readouts measured in each system. The Y-axis represents a log-transformed ratio of the biomarker readouts for the drug-treated sample (n=1) over vehicle controls (n≥6). The grey region around the Y-axis represents the 95% significance envelope generated from historical vehicle controls. Biomarker activities are annotated when 2 or more consecutive concentrations change in the same direction relative to vehicle controls, are outside of the significance envelope, and have at least one concentration with an effect size>20% (|log 10 ratio|>0.1). Biomarker key activities are described as modulated if these activities increase in some systems, but decrease in others. Cytotoxicity is indicated on the profile plot by a thin black arrow above the X-axis, and antiproliferative effects are indicated by a thick grey arrow. Cytotoxicity and antiproliferative arrows only require one concentration to meet the indicated threshold for profile annotation. In the BioMAP procedure, "cytotoxicity" is defined where protein production in the assay is reduced to below 50%, and in some instances does not necessarily mean that cells are dying.

The yeast extract composition had detectable cytotoxicity (thin black arrows) in the following systems at 12% (SAg, BT) and 6.2% (SAg). A large dose response was observed between the top concentrations (12%, 6.2%) compared to the lower two concentrations (3.1%, 1.6%), which may be due to the engagement of additional targets at higher concentrations. Systems with detectable cytotoxicity were annotated at non-cytotoxic concentrations.

The yeast extract composition was shown to be antiproliferative to human primary B cells (6.2%, 3.1%, 1.6%), T cells (3.1%), coronary artery smooth muscle cells (12%, 6.2%, 3.1%), endothelial cells (12%, 6.2%, 3.1%, 1.6%) and fibroblasts (12%, 6.2%) (grey arrows). The yeast extract composition mediated changes in key biomarker activities are listed by biological and disease classifications: inflammation-related activities (decreased Eotaxin 3, MCP-1, MIP-1α, I-TAC, ICAM-1, MIG, IP-10, sPGE2, IL-6, E-selectin, VCAM-1, SAA, sTNFα, P-selectin; modulated IL-8, IL-1α); immunomodulatory activities (decreased CD40, sIgG, M-CSF, sIL-17A, sIL-17F, sIL-2, sIL-10, HLA-DR, CD38, CD69); tissue remodeling activities (decreased Collagen I, TIMP-1, CD90, Collagen III, aSMA, bFGF, MMP-1, MMP-3, PAI-1, uPAR, Kerb/18, MMP-9; modulated TIMP-2, tPA, uPA); hemostasis-related activities (decreased TF; increased TM); and other activities (decreased LDLR).

At the lowest two concentrations, the yeast extract composition was active with 32 annotated readouts. It was not cytotoxic at these concentrations. The yeast extract composition was shown to be antiproliferative to human primary B cells (3.1%, 1.6%), T cells (3.1%), coronary artery smooth muscle cells (3.1%) and endothelial cells (3.1%, 1.6%), and to mediate changes in key biomarker activities: inflammation-related activities (decreased Eotaxin 3, E-selectin, VCAM-1, sTNFα, I-TAC, MIG, IL-6, P-selectin; increased IL-8, IL-1α); immunomodulatory activities (decreased CD40, sIL-10, sIgG, M-CSF, HLA-DR, CD38, sIL-17F, sIL-2); and tissue remodeling activities (decreased PAI-1, uPAR, MMP-9; increased tPA, uPA).

The therapeutic yeast extracts demonstrated profile similarity with Radicicol, Valproic Acid, and JQ1, at differing concentrations. Similar BioMAP profiles points towards similarities in mechanism of action.

At the two highest concentrations tested, HSP90 inhibitor Radicicol had the most similar compound profile to Therapeutic Yeast Extracts with Pearson's correlation coefficients (12% TYE r=0.749, 6.2% TYE r=0.738). The BET inhibitor JQ1 had the second most similar profile at high concentrations with Pearson's correlation coefficients of (12% TYE r=0.633, 6.2% TYE r=0.697). HDAC inhibitor Valproic Acid was the top match for therapeutic yeast extracts at low concentration (3.1% TYE r=0.789). Taken together, these results suggest that TYE (therapeutic yeast extracts) is playing a significant role in the regulation of HSP90. It demonstrates profile similarities to three drugs which all impact HsP90 expression. Like Radicicol, TYE may bind HSP90 directly, inhibiting its function like Valproic Acid, TYE may inhibit HDAC6 which is required for the activation of HSP90 expression. Or like JQ1, TYE may prevent the reading of acetylated histones by BET proteins, which precedes HDAC6 activation of HSP90 expression.

Figure 2:
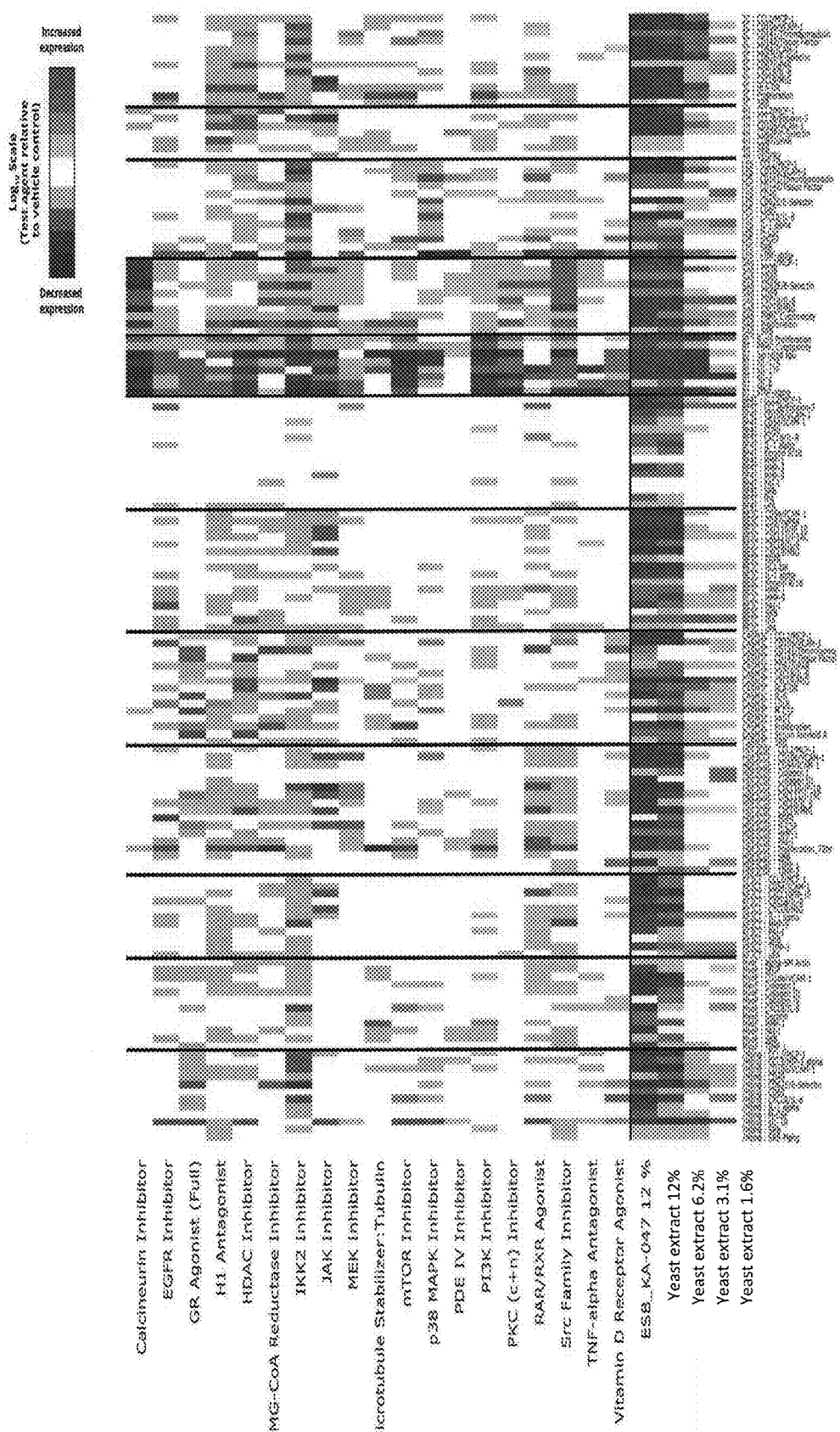
FIG. 2 depicts a HeatMap analysis result for a yeast extract composition of the present invention in comparison to 19 consensus mechanism class profiles.

FIG. 2 shows a HeatMAP analysis of the 148 biomarker readouts (rows) within the Diversity PLUS panel by in comparison to 19 consensus mechanism class profiles (columns). Horizontal grey lines separate the 12 Diversity PLUS systems, while the vertical grey line separates the therapeutic yeast extracts from the 19 consensus mechanism profiles. Biomarker activities outside of the significance envelope are red if protein levels are increased, blue if protein levels are decreased and white if levels are within the envelope or unchanged. Darker shades of color represent greater change in biomarker activity relative to vehicle control. These class profiles were generated from a large reference dataset. This Mechanism HeatMAP analysis informs on the regulatory mechanisms controlling increases or decreases in each of the biomarker readouts. For example, the increase in IL-8 in the 1 Mphg System is a feature of mTOR inhibitors, RAR/RXR agonists and VDR agonists.

Example 6. Fermentation

*Saccharomyces cerevisiae* yeast is fermented under standard conditions, using nutrients familiar to those skilled in the art, with a common sugar source, such as, but not limited to, molasses. The fermentation comprised one or more fermentation steps (e.g., two, three, four, or more), optionally including at least one anaerobic condition, where each step comprised a fermentation at a desired temperature and for a desired duration, and where nutrient levels were adjusted, as needed in each fermentation step, for example a 20% by weight sugar was used at 28-30° C. temperature for 2 to 24 hours. When more than one fermentation is performed, the temperature and duration of each step may be the same or different. Temperatures of between 15° C. and 56° C. were employed in each step, with the total time of fermentation being between 1 hour and up to about 2 weeks. In addition to fermentation, the yeast were subjected to stresses, the fermentation liquid was separated from solids, the necessary amount of undesirable residue was removed from the liquid to improve the therapeutic effects, the yeast were disrupted, and where the constituents in the resulting extract comprise a therapeutic level of one of more of the following: (a) GPCR antagonist agents (e.g., histamine receptor antagonist agents, (b) a therapeutic level of Substance P receptor antagonist agents, (c) cytokine receptor antagonist agents, (d) HSP90 inhibitor agent, (e) HDAC inhibitor agent, (f) BET inhibitor agent and where about 98% of these constituents in totality had a molecular weight below about 4 KDa, and then the extract was stabilized with 0.2% sodium benzoate and 0.1% potassium sorbate and pH adjusted to 4.5 with citric acid. Strong alkali conditions were avoided and pH was maintained under 8.0 in all processes.

Example 7. Oxygen Uptake Activation and Mild Uncoupling of Oxidative Phosphorylation in Skin Fibroblasts To reveal the nature of the uncoupling agent by oxygen uptake activation in animal cells, this effect was studied in adult human skin fibroblast cell culture in which ATP-synthase has been blocked by oligomycin. The effect of the therapeutic yeast extract was compared with a standard ionophore uncoupler of oxidative phosphorylation p-trifluoromethoxyphenylhydrazone (FCCP). The latter provides about a 10-fold activation of oxygen consumption rate in oligomycin-blocked fibroblasts. An activation was also achieved in the presence of the therapeutic yeast extracts. Without being bound to any particular theory, it is postulated that the likely mechanism of the enhanced oxygen uptake is through proton leak across the mitochondrial membrane, which results in the lifting of the phosphorylation control over electron transport. These data appear to be the first indication of a mild uncoupling effect of yeast extracts in these cells. Uncoupling is considered as an equivalent of caloric restriction, and the latter as an approach to rejuvenation, and in that context may be relevant in skin rejuvenation, reduction of inflammation, wrinkles and alike.

Example 8. Testing Therapeutic Yeast Extracts and Related Materials in Treatment of Psoriasis and Eczema Case #1: Tests were conducted with a formulation comprising 10% therapeutic yeast extracts (17.5 mg/mL protein) in an herbal cream base [www.makingcosmetics.com/Herbal-Cream-Base_p_67.html]. The subject was a 57-year-old male with plaque psoriasis on both elbows, forearms, hands, knees and back side of knees, ankle and foot areas. The application resulted in relief of itch after several minutes following the application. Though the psoriasis spots were still evident after three weeks of use, the severity of the skin condition improved notably. Moisturizers were used from time to time to augment the application of the therapeutic yeasts extract formulation.

Case #2: A 27-year old female suffered from plaque psoriasis, most pronounced at her elbows. She applied the therapeutic yeast extracts solution as described above in Example 2 but stabilized with 0.1% Kathon™ CG (Dow Chemical) preservative and no other additives. There was an immediate reduction, or elimination of itching and elimination of the "pain" and a pleasant feel. The psoriasis was notably reduced, with about 70% reduction in scaling after only three days of use, and further reduction with continued use.

Case #3: A 57 year old male with psoriasis and eczema applied the formulation from Example 1 and itch relief was immediate, quicker for eczema than psoriasis. With daily application for many weeks the skin condition improved significantly. In addition, the subject substituted the extract in some instances with 1% hydrocortisone cream and, in other parts of the body at different times, depending on the condition, applied prescription Clobetasol Propionate Cream, U.S.P. 0.05%. After 2 or 3 days of just using the corticosteroid creams, the skin had a dramatic improvement in condition. Afterward, the subject continued with application of the therapeutic yeast extract. A synergy was noted, while at the same time reducing the amount of exposure to the corticosteroids, which reduces the potential negative side effects.

Case #4: A 75-year old male with psoriasis in the back of the lower scalp at the neckline was provided with an analog of a shampoo he routinely used to wash his hair, which had not mitigated the dry, itchy patches of skin prior to adding the extract, modified with 7.8% therapeutic yeast extracts. The modified shampoo was used on a daily basis. After one week, it was noted that the itching was gone. Some redness remained. But hydrocortisone was not used on the scalp. Continued, regular use has prevented any flare-ups. The scaly, dry flakes had all but disappeared.

Case #5. Eczema Clinical Study Results

TABLE 7

Sample skin formulation.

| Ingredients | % |
| --- | --- |
| Therapeutic Yeast Extract | 0.5-50% |
| Glycerin | 1-20% |
| Hydroxyethylcellulose | 0.5-5% |
| Decyl Glucoside | 0.25-10% |
| Sodium Belzoate | 0..1-1% |
| Potassium Sorbate | 0.1-1% |
| Citric Acid up to | pH 3-7 |
| Water | To 100% |

24 out of 35 subjects that suffered from eczema reported "immediate" relief from itch when treated using the methods described herein where the formulation used in the tests comprised no ingredients that are known in the art to relive itch, such as colloidal oatmeal or corticosteroids and comprised the therapeutic yeast extract of Example 1 that further comprised a thickening agent and a surfactant. The remainder 14 out of 35 reported itch relief in under 3 minutes in the first application. On a scale from 1 to 10, 1 being best and 10 being worst, the subjects scored various clinical outcomes. The average scores are reported below.

TABLE 8

Summary of eczema studies.

| Condition | Before | After |
| --- | --- | --- |
| Severity of itch and inflammation | 7.8 | 1.9 |
| Severity of dryness | 7.7 | 1.8 |
| Skin condition after 3 weeks of 2 to 3 times daily application | N/A | 1.9 |

After the application of the therapeutic yeast extract formulation for 3 weeks, 1% hydrocortisone was applied daily for 3 days. The subjects where then asked whether they agreed or disagreed with the following statement: "The hydrocortisone application showed further improvement in the skin condition affected by eczema." The responses were: 68.6% agreed; 20% neither agreed nor disagreed; and 11.4% disagreed. There was an overwhelming positive response in some synergy with using a corticosteroid in small amounts in conjunction with the therapeutic yeast extracts based formulation.

Example 4. Acne Pilot Study Results 10 subjects with acne vulgaris tested a face wash that comprised the therapeutic yeast extracts, contained no ingredients typically used in the art in acne treatment, such as peroxides, etc., with twice daily washing for 3 weeks. At the conclusion of the study, the subjects were asked whether they agreed or disagreed with a set of statements. The results were as follows:

TABLE 9

Summary of acne studies.

| Statement | Agree | Disagree | Neither agree nor disagree |
|---|---|---|---|
| I noticed a significant improvement in the quality/health of my skin due to acne | 50% | 30% | 20% |
| The Face Wash reduced the appearance of whiteheads | 70% | 30% | 0% |
| The Face Wash reduced the appearance of inflamed pimples | 60% | 30% | 10% |
| The Face Wash reduced the appearance of blackheads | 50% | 30% | 20% |
| The overall condition of my skin improved after using the Face Wash | 70% | 30% | 0% |
| After 3 weeks, whiteheads appeared to be reduced | 90%†; 50%‡ | | |
| After 3 weeks, the red pimples seemed to be reduced | 90%†; 50%‡ | | |
| After 3 weeks of use, my blackheads appeared to be reduced | 90%†; 40%‡ | | |

†Subjects had at least some reduction.
‡Over half were gone

Example 8. Dandruff Pilot Study 10 subjects with dandruff tested a Dandruff Shampoo that comprised the therapeutic yeast extracts, with once daily washing for 3 weeks. No other ingredients known in the art to relieve dandruff were used in the formulation, only surfactants (<1%), thickening agent and stabilizers. The shampoo contained no conditioners. At the conclusion of the study, the subjects were asked whether they agreed or disagreed with a set of statements. The results were as follows:

TABLE 10

Summary of dandruff studies.

| Statement | Agree | Disagree | Neither agree nor disagree |
|---|---|---|---|
| The Shampoo helped reduce the itching sensation on my scalp | 63.6% | 36.4% | 0% |
| The Shampoo helped reduce the appearance of dry flakes on my scalp due to dandruff | 72.7% | 0% | 27.3% |
| The condition of my hair is softer after using the Shampoo | 54.5% | 27.3% | 18.2% |
| My dandruff has not returned since using the Shampoo | 63.6% | 18.2% | 18.2 |
| The Shampoo reduced flaking of dry skin from the scalp when rubbed | 27%†; 54.5%‡; 9.1%⹋ | 9.1 | |

†Completely
‡Mostly/Somewhat
⹋Slightly

Example 9. Athlete's Foot Pilot Study 10 subjects with athlete's foot tested an athlete's foot formulation that comprised the therapeutic yeast extracts, from Example 3, Case #5, with once daily application for 2 weeks. No other ingredients known in the art to relive athlete's foot, such as antifungal agents, were used in the formulation, except for surfactants (<1%), thickening agents and stabilizers. At the conclusion of the study, the subjects were asked whether they agreed or disagreed with a set of statements. The results were as follows:

TABLE 11

Summary of athlete's foot study.

| Statement | Agree | Disagree | Neither agree nor disagree |
|---|---|---|---|
| The formulation felt soothing shortly after the first application | 83.4% | 8.3% | 8.3% |
| I felt overall the formulation helped relieve my Athlete's Foot | 83.4% | 0 | 16.6% |
| I feel the formulation helped relieve symptoms quickly | 58.3% | 8.3% | 33.3% |

Example 10. Wound Treatment

A 56-year old male cut the skin at the base of the second and third fingers. After applying the therapeutic yeast extracts described herein, the opening stung a little for about two minutes. Subsequently, the skin opening appeared to be healing. No scar or scab was formed. The same male had a persistent cut at the base of the fifth (pinky) and fourth fingers. The disclosed therapeutic yeast extracts composition was used with one application, and had a stinging sensation for about two minutes. Within a couple of hours, it had closed and healed in a few days. The skin had been unable to heal for weeks prior to the therapeutic yeast extract application. Multiple different creams had been tried, which only provided some comfort and hydrating, but not healing.

Example 11. Wound Healing Tests

Wound healing studies were performed on wild-type mice with normal wound healing properties and mice that were genetically modified to be diabetic. Each cohort included 36 mice for a total of 72. Mice were anesthetized and two 6 mm full thickness wounds were surgically performed on each mouse for a grand total of 184 wounds (72 wound in each cohort). The therapeutic yeast extract solution used in Example 6, as described herein was applied to each wound daily. Mice were sacrificed on days 7, 14 and 28 after the wounds were created. The wounds were then histologically analyzed using a variety of techniques. Percentage of wound healing was analyzed by measuring the gap in epithelial wound edges over the initial diameter of the wound. Results indicate that there was no statistically significant difference for healthy, standard mice, as expected, since in normal mice natural healing is fairly efficient. However, and more significantly, in diabetic mice, where a wound is compromised by the diabetic condition, there was a significant improvement in wound healing as seen in the table below.

Diabetic Mice Wound Healing

TABLE 12

Summary of wound healing study.

| No. of Days since Application | Control | Vehicle | yeast extracts Solution |
|---|---|---|---|
| 7 days | 13.75% | 21.25% | 14.38% |
| 14 days | 39.38 | 68.75 | 84.38 |
| 28 days | 100 | 100 | 100 |

The epidermal thickness between the control and yeast protein group was statistically significant at day 7, 14, and 28 (p=0.02, 0.002, 0.000 respectively). Fibroblast density between the control and yeast extract groups was statistically significant at day 7 and 28 (p=0.002 and 0.000). Blood vessel content was significantly different between control and yeast extract groups at day 7 and 14 (p=0.01, 0.005). Collagen content in the yeast extract group was significantly greater compared to the control at days 7, 14, and 28 (p=0.00, 0.003, 0.009).

For the diabetic mice, epidermal thickness was significantly different in control vs. yeast groups at day 7 and 28 (p=0.002, 0.001). Collagen content was significantly different in control vs. yeast at day 7 (p=0.05).

The diabetic mice demonstrated delayed wound healing across all groups at day 7 with 13.8%, 21%, and 14.4% for control, vehicle and yeast groups, respectively. At day 14 control, vehicle and yeast groups demonstrated 39.4%, 68.8%, and 84.4% of wound healing, respectively.

Example 13. Sample Formulation 1

The following sample formulation was prepared for sunburn relief and acne face wash applications. Acne facial wash/cleansing (prototype B) was used by a 17-year old female for three weeks on a daily basis, with significant improvement of facial skin condition.

TABLE 13

Sample formulation for skin treatment.

| Ingredients | A Sunburn Relief % | B Acne Face Wash % |
|---|---|---|
| Therapeutic yeast extract | 0.5 | 2 |
| Lactic acid | 1.5 | 5 |
| Propylene glycol | 2 | 0.45 |
| Decyl glucoside | 0.25 | 0.25 |
| Kathon™ (preservative) | 0.05 | 0.05 |
| Water | 95.7 | 92.25 |
| Total | 100 | 100 |
| 0.1N NaOH <0.1% | pH 4.0 | pH 5.5 |

Example 14. Hemorrhoid Pilot Study

A total of 10 subjects evaluated a formulation that comprised the extract used in Example 6, with glycerin, under 1% of the following: surfactant, and 2 each thickening agents for viscosity adjustment, and preservatives and contained no ingredients known to be active in reducing hemorrhoid symptoms. 9 of 10 subjects reported nearly total relief of various symptoms of hemorrhoids in a 14 day evaluation study, where the YE formulation was applied at least once per day.

10 subjects—Severity of symptoms at noted time periods (Ave/Std Dev) Severity level, 1 Best, 10 Worst at the noted time of trial period

TABLE 14

Summary of hemorrhoid study.

| | Pain | Itch | Burning | Soreness |
|---|---|---|---|---|
| Prior to Application | 4.70/2.72 | 4.50/1.75 | 3.90/1.76 | 5.20/2.09 |
| 15 minutes after application | 3.20/2.32 | 3.00/1.73 | 2.40/1.50 | 3.20/2.40 |
| 3 days of application | 2.50/1.96 | 2.10/1.37 | 2.00/1.26 | 2.70/1.90 |
| 7 days of application | 1.80/1.25 | 1.80/1.25 | 1.60/1.20 | 1.70/1.19 |
| 14 days of application | 1.50/120 | 1.60/1.20 | 1.40/1.20 | 1.40/1.20 |
| Prior to Application, 9 only* | 4.44 | 4.22 | 3.90 | 5.20 |
| 7 days, 9 subjects only* | 1.44 | 1.44 | 1.22 | 1.33 |
| 14 days, 9 subjects only* | 1.11 | 1.22 | 1.00 | 1.00 |

*Only one subject saw minimal relief, from 7 to 5 at 7 and 14 days and those values were omitted in these rows.

The 10 subjects with hemorrhoids further provided their opinion on the following statements. (SA—Strongly Agree, A—Agree, N—Neither Agree or Disgree, D—Disagree)

The product helped relieve itching due to hemorrhoids—6 SA-4 A

The product helped relieve burning due to hemorrhoids—6 SA-3 A-1 N

The produce helped to relieve soreness due to hemorrhoids—6 SA-2 A-2 N

The product helped to make my bowel movements less painful—5 SA-2 A-3 N

The produce gave rapid soothing pain relief of my hemorrhoid pain-5 SA-5 A

The product temporarily helped shrink my hemorrhoids—5 SA-2 A-2 N-1 D

The product helped relieve pain due to hemorrhoids—5 SA-4 A-1 N

The average number of days reported by the subjects to shrink hemorrhoids was 4.375 days.

Example 15

Dry Eye. A 43 year old male with chronic dry eye condition had used various eye drops. He applied a small amount of the therapeutic yeast extract formula to the inside of the lower eyelid and had an immediate feeling of relief. The male also reported that this was an allergic type of reaction and that the eye had itched.

Example 16. Herpes Treatment

A teenage girl had herpes simplex lesions, with typical symptoms of pain, inflammation and scab formation during healing. Applying the therapeutic yeast extract had an immediate soothing effect. The inflammation was reduced and the scab formation was significantly reduced. Application was done multiple times daily as symptoms persisted.

What is claimed:

1. A topical skin composition, comprising:
   an extract from yeast, wherein the extract from yeast comprises:
   (a) an anti-inflammatory agent produced by the yeast, and
   (b) an uncoupling agent active in human cells produced by the yeast; and
   an added surfactant;
   an added thickening agent; and
   an added preservative,
   wherein yeast proteinaceous material comprises from 90% to 98% of the total non-volatile solids in the composition.

2. The composition of claim 1 where the anti-inflammatory agent is an anti-itch agent.

3. The compositions of claim 1, wherein the anti-inflammatory agent, or the anti-itch agent is a histamine receptor antagonist agent.

4. The composition of claim 1, wherein the anti-inflammatory agent comprises one or both of a G Protein Coupled Receptor (GPCR) antagonist agent and a cytokine receptor antagonist agent.

5. The composition of claim 1, wherein the anti-inflammatory agent comprises one or more of a Heat Shock Protein 90 (HSP90) inhibitor agent, a histone deacetylase (HDAC) inhibitor agent and a Bromodomain and Extra-Terminal motif (BET) inhibitor agent.

6. The composition of claim 1, wherein the composition is antiproliferative to one or more of human primary B cells, endothelial cells, fibroblasts, and coronary artery smooth muscle cells in an in vitro cell based proliferation assay.

7. The composition of claim 4, wherein at least about 98% of the cytokine receptor antagonist agent present in the composition, and optionally one or both of the GPCR antagonist agent and the uncoupling agent, is under a molecular weight of about 4,000 daltons.

8. The composition of claim 7, wherein at least about 90% the cytokine receptor antagonist agent, and optionally one or both of the GPCR antagonist agent and the uncoupling agent, present in the composition is soluble.

9. The composition of claim 1, wherein the extract is a Saccharomyces cerevisiae extract.

10. The composition of claim 1, wherein the yeast extract comprises soluble constituents, is substantially colorless and odorless, and is devoid of insoluble materials that may be separated from soluble matter by centrifugation.

11. The compositions of claim 1, wherein the yeast extract is substantially free of undesirable residue.

12. The composition of claim 3, wherein the histamine receptor antagonist is an antagonist for one or more of H1R, H2R, H3R and H4R histamine receptors.

13. The composition of claim 4, wherein the cytokine receptor antagonist agent is an antagonist for a receptor of a cytokine selected from the group consisting of TNF-alpha, interferon-gamma, Granulocyte-macrophage colony-stimulating factor (GM-CSF), IL-1, IL-2, IL-4, IL-5, IL-6, IL-12, IL-13, IL-17, IL-22, IL-31, IL-33.

14. The composition of claim 4, wherein the GPCR antagonist agent is a Substance P receptor antagonist agent.

15. The composition of claim 4, wherein the GPCR antagonist agent, the cytokine receptor antagonist agent, and the uncoupling agent are soluble in the composition, and wherein about 98% of the GPCR antagonist agent, the cytokine receptor antagonist agent, and the uncoupling agent are under a molecular weight of about 4,000 daltons.

16. The composition of claim 1 that further comprises: a preservative, an antimicrobial agent, an emollient, a fragrance, or combinations thereof.

17. A method of obtaining a therapeutic yeast extract of claim 1, comprising:
   (a) fermenting yeast, wherein the fermenting step comprises more than one fermentation procedure, and wherein the fermenting step optionally comprises one or both of the following steps:
   the fermenting step optionally comprises at least one fermentation procedure under anaerobic conditions, and
   the fermenting step optionally comprises at least one fermentation procedure at a temperature greater than 30° C.;
   (b) subjecting the yeast to a stress;
   (c) disrupting or lysing the yeast;
   (d) purifying the yeast to substantially remove undesirable residue; and
   (e) separating insoluble material from the liquid soluble materials.

18. A method according to claim 17, wherein the fermenting step comprises a total fermentation time of between 1 hour and to about 2 weeks.

19. A method of treating inflammation or itching of the skin of a subject in need thereof, comprising:
   topically administering a composition according to one of claim 1 to an affected area the subject.

20. The composition of claim 1, wherein the composition further comprises one or more ingredients selected from the group consisting of oatmeal, cannabinoids, and glycerin.

21. The composition of claim 20, wherein the composition further comprises oatmeal.

* * * * *